United States Patent [19]

Zhang et al.

[11] Patent Number: 5,817,749
[45] Date of Patent: Oct. 6, 1998

[54] PROCESSES AND INTERMEDIATE COMPOUNDS FOR THE PREPARATION OF PLATELET GLYCOPROTEIN IIB/IIIA INHIBITORS

[75] Inventors: Lin-Hua Zhang, Wilmington, Del.; Philip Ma, Chadds Ford; William Frank DeGrado, Moylan, both of Pa.

[73] Assignee: DuPont Pharmaceuticals Company, Wilmington, Del.

[21] Appl. No.: 371,624

[22] Filed: Jan. 12, 1995

Related U.S. Application Data

[63] Continuation of Ser. No. 38,434, Mar. 29, 1993, abandoned.
[51] Int. Cl.$^6$ ................... C07K 7/50; C07K 1/10
[52] U.S. Cl. ................ 530/317; 530/330; 530/333; 530/339
[58] Field of Search .............. 530/317, 330, 530/333, 339; 514/11

[56] References Cited

U.S. PATENT DOCUMENTS

| | | | |
|---|---|---|---|
| 5,192,746 | 3/1993 | Lobl et al. | 514/11 |
| 5,322,931 | 6/1994 | Hubbs et al. | 530/333 |
| 5,384,309 | 1/1995 | Barker et al. | 530/317 |

FOREIGN PATENT DOCUMENTS

| | | |
|---|---|---|
| 0192135 | 8/1986 | European Pat. Off. . |
| 0422937 | 4/1991 | European Pat. Off. . |
| 0425212 | 5/1991 | European Pat. Off. . |
| 0444898 | 9/1991 | European Pat. Off. . |
| 0406428 | 1/1992 | European Pat. Off. . |
| 289543 | 5/1991 | German Dem. Rep. . |
| 103252 | 2/1993 | Israel . |
| WO9207870 | 5/1992 | WIPO . |
| WO 93/07170 | 4/1993 | WIPO . |
| WO9415958 | 7/1994 | WIPO . |

OTHER PUBLICATIONS

Miller, A.E. and Bischoff, J.J., "Facile Conversion of Amino Acids to Guanidino Acids", Journal of Synthetic Organic Chemistry, 1986 No. 9, 777–779.

Eberhard Schroder and Klaus Lubke, "The Synthesis of Cyclis peptides", The Peptides, 1965, vol. I, 271–272.

*Primary Examiner*—Cecilia J. Tsang
*Assistant Examiner*—Anish Gupta
*Attorney, Agent, or Firm*—G. Jess Boudreaux; David H. Vance

[57] ABSTRACT

This invention provides processes for the synthesis of platelet glycoprotein IIb/IIIa inhibitors and intermediate compounds useful in said processes. The compounds afforded by this invention have the formula:

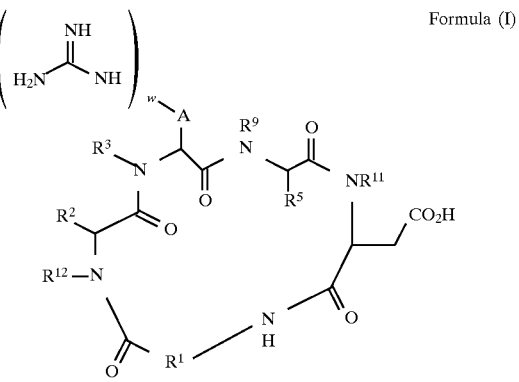

Formula (I)

19 Claims, No Drawings

PROCESSES AND INTERMEDIATE COMPOUNDS FOR THE PREPARATION OF PLATELET GLYCOPROTEIN IIB/IIIA INHIBITORS

This is a continuation of application Ser. No. 08/038,434, filed Mar. 29, 1993 now abandoned.

FIELD OF THE INVENTION

This invention relates to a process for the synthesis of platelet glycoprotein IIb/IIIa inhibitors and to intermediate compounds useful in said process.

BACKGROUND OF THE INVENTION

Activation of platelets and the resulting platelet aggregation and secretion of factors by the platelets have been associated with different pathophysiological conditions including cardiovascular and cerebrovascular thromboembolic disorders, for example, the thromboembolic disorders associated with unstable angina, myocardial infarction, transient ischemic attack, stroke, atherosclerosis and diabetes. The contribution of platelets to these disease processes stems from their ability to form aggregates, or platelet thrombi, especially in the arterial wall following injury.

Platelets are known to play an essential role in the maintenance of hemostasis and in the pathogenesis of arterial thrombosis. Platelet activation has been shown to be enhanced during coronary thrombolysis which can lead to delayed reperfusion and reocclusion. Clinical studies with aspirin, ticlopidine and a monoclonal antibody for platelet glycoprotein IIb/IIIa provide biochemical evidence for platelet involvement in unstable angina, early stage of acute myocardial infarction, transient ischemic attack, cerebral ischemia, and stroke.

Platelets are activated by a wide variety of agonists resulting in platelet shape change, secretion of granular contents and aggregation. Aggregation of platelets serves to further focus clot formation by concentrating activated clotting factors in one site. Several endogenous agonists including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane $A_2$ synthetase inhibitors or receptor antagonists, which act against thromboxane $A_2$; and hirudin, which acts against thrombin.

Recently, a common pathway for all known agonists has been identified, namely platelet glycoprotein IIb/IIIa complex (GPIIb/IIIa), which is the membrane protein mediating platelet aggregation. A recent review of GPIIb/IIIa is provided by Phillips et al. (1991) Cell 65: 359–362. The development of a GPIIb/IIIa antagonist represents a promising new approach for antiplatelet therapy. Recent studies in man with a monoclonal antibody for GPIIb/IIIa indicate the antithrombotic benefit of a GPIIb/IIIa antagonist.

There is presently a need for a GPIIb/IIIa-specific antiplatelet agent which inhibits the activation and aggregation of platelets in response to any agonist. Such an agent should represent a more efficacious antiplatelet therapy than the currently available agonist-specific platelet inhibitors.

GPIIb/IIIa does not bind soluble proteins on unstimulated platelets, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the Arg-Gly-Asp (RGD) recognition sequence which is common to the adhesive proteins that bind GPIIb/IIIa.

Several RGD-containing peptides and related compounds have been reported which block fibrinogen binding and prevent the formation of platelet thrombi. For example, see Cadroy et al. (1989) J. Clin. Invest. 84: 939–944; Klein et al. U.S. Pat. No. 4,952,562, issued 8/28/90; European Patent Application EP 0319506 A; European Patent Application EP 0422938 A1; European Patent Application EP 0422937 A1; European Patent Application EP 0341915 A2; PCT Patent Application WO 89/07609; PCT Patent Application WO 90/02751; PCT Patent Application WO 91/04247; and European Patent Application EP 0343085 A1.

Compounds of formula (I) are difficult to prepare. For example, the process described in U.S. patent application Ser. No. 07/949,085 uses modified solid phase methodology in the synthesis. This method is not applicable to bulk drug preparations. Thus, there is a need for a process capable of providing these compounds that utilizes readily available starting materials, cheaper coupling reagents and techniques that do not require high dilution. It is an objective of the present invention to provide a process for the preparation of platelet glycoprotein IIb/IIIa inhibitors. It is also an objective of the present invention to provide intermediate compounds useful in said process. Finally, it is an objective of this invention to provide processes for the prepartion of said intermediate compounds.

DETAILED DESCRIPTION OF THE INVENTION

This invention is directed to a process for the preparation of compounds of formula:

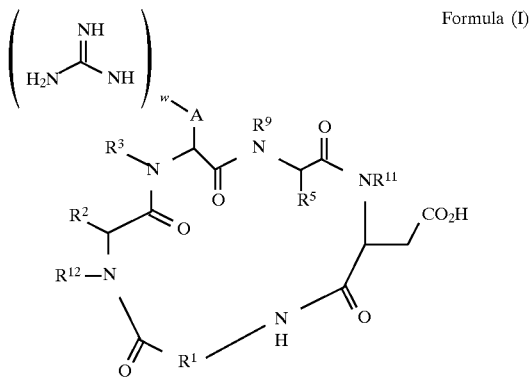

Formula (I)

comprising the steps of:

(a) coupling an amino tripeptide of formula:

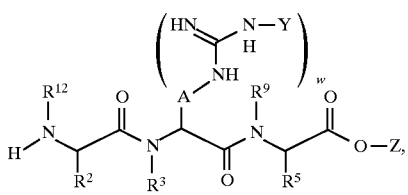

wherein Z is a carboxylic acid protecting group and Y is an amine protecting group, with a carboxylic acid derivitive of formula:

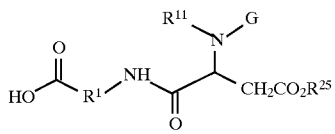

wherein G is an amine protecting group, to produce a protected linear peptide of formula:

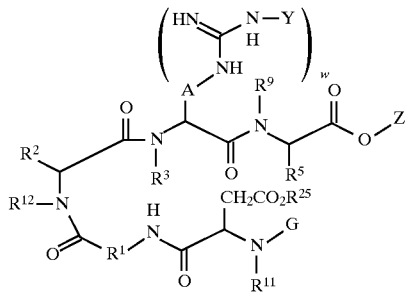

(b) removing the Z and C protecting groups of the product of Step (a) in one step to produce a deprotected linear peptide of formula:

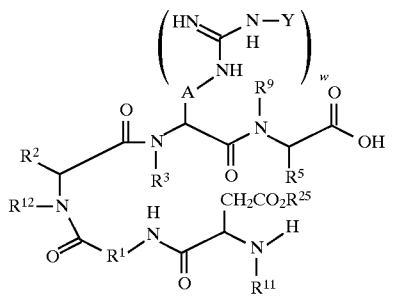

(c) cyclizing the deprotected linear peptide of Step (b) to produce a cyclic peptide of formula:

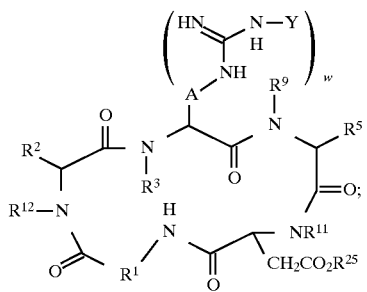

(d) removing the Y group and the t-butyl group of the product of Step (c) to produce an amine of formula (I):
wherein:
w is 0 or 1;
$R^1$ is

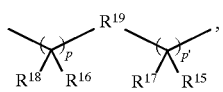

wherein:
p and p' are 0 or 1;

$R^{19}$ is a $C_6$–$C_{14}$ saturated, partially saturated, or aromatic carbocyclic ring system or heterocyclic ring system composed of at least 1–3 heteroatoms selected from N, O, S; all these ring systems may be optionally substituted with 0–2 $R^7$;

$R^{17}$ and $R^{16}$ are independently selected from the group: hydrogen;
$C_1$–$C_4$ alkyl, optionally substituted with halogen;
$C_1$–$C_2$ alkoxy; benzyl;

$R^{15}$ and $R^{18}$ are independently selected from the group: hydrogen,
$C_1$–$C_8$ alkyl substituted with 0–2 $R^8$,
$C_2$–$C_8$ alkenyl substituted with 0–2 $R^8$,
$C_2$–$C_8$ alkynyl substituted with 0–2 $R^8$,
$C_3$–$C_8$ cycloalkyl substituted with 0–2 $R^8$,
$C_6$–$C_{10}$ bicycloalkyl substituted with 0–2 $R^8$,
aryl substituted with 0–2 $R^{13}$,
a heterocyclic ring system composed of 5–10 atoms including 1–3 nitrogen, oxygen, or sulfur heteroatoms, optionally substituted with 0–2 $R^{13}$;

$R^{15}$ and $R^{11}$ can alternatively join to form a 5–8 membered carbocyclic ring substituted with 0–2 $R^{13}$, when $R^{17}$ is H;

$R^7$ is independently selected at each occurrence from the group:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2R^{20}$, sulfonamide, formyl, $C_3$–$C_6$ cycloalkoxy, —OC(=O)R20, —C(=O)R20, —OC(=O)OR$^{20}$, —OR$^{20}$, —$CH_2OR^{20}$, $C_1$–$C_4$ alkyl optionally substituted with —$NR^{20}R^{21}$;

$R^8$ is independently selected at each occurrence from the group:
=O, F, Cl, Br, I, —$CF_3$, —CN, —$CO_2R^{20}$, —C(=O)$NR^{20}R^{21}$, —$CH_2OR^{20}$, —OC(=O)R20, —$CH_2NR^{20}R^{21}$, —$NR^{20}R^{21}$;

$R^{13}$ is independently selected at each occurrence from the group:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2R^{20}$, sulfonamide, formyl, $C_3$–$C_6$ cycloalkoxy, —OC(=O)R20, —C(=O)R20, —OC(=O)OR$^{20}$, —OR$^{20}$, —$CH_2OR^{20}$, $C_1$–$C_4$ alkyl (substituted with —$NR^{20}R^{21}$);

$R^{20}$ is independently selected at each occurrence from the group:
H, $C_1$–$C_7$ alkyl, aryl, —($C_1$–$C_6$ alkyl)aryl, or $C_3$–$C_6$ alkoxyalkyl;

$R^{21}$ is independently selected at each occurrence from the group:
H, $C_1$–$C_4$ alkyl, or benzyl;

$R^{11}$ is H or $C_1$–$C_8$ alkyl;

$R^{12}$ is H or C1–C8 alkyl;

$R^2$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, $(CH_2)_sNHC(=NH)(NH_2)$, $(CH_2)_sNHR^{21}$, wherein s = 3–5;

$R^{12}$ and $R^2$ can be taken together to form —$(CH_2)_t$— wherein t=2–4, or —$CH_2SC(CH_3)_2$—;

$R^3$ is H or $C_1$–$C_8$ alkyl;

A is selected from the group:

—$C_1$–$C_7$ alkyl—,

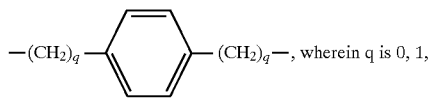, wherein q is 0, 1,

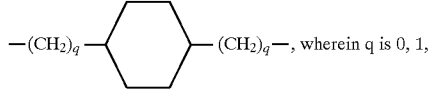, wherein q is 0, 1,

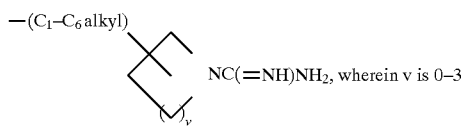 NC(=NH)$NH_2$, wherein v is 0–3 and provided that w=0,
—$(CH_2)_mO$—($C_1$–$C_4$ alkyl)—, wherein m=1,2,
—$(CH_2)_mS$—($C_1$–$C_4$ alkyl)—, wherein m=1,2;
$R^3$ and A may also be taken together to form

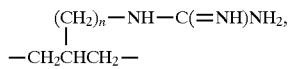

wherein n=0–1 and provided that w=0;
$R^9$ is H, $C_1$–$C_8$ alkyl; and
$R^5$ is H, $C_1$–$C_8$ alkyl.

In a preferred embodiment, the above described process provides compounds of formula (I) wherein:
$R^{19}$ is selected from:

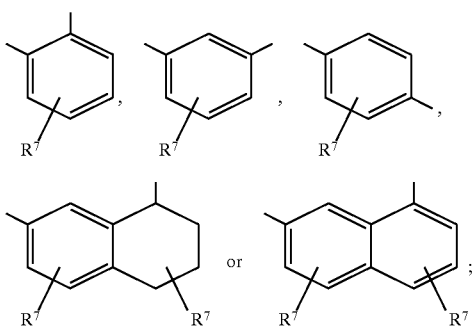

$R^{15}$ and $R^{18}$ are independently selected from H, $C_1$–$C_4$ alkyl, phenyl, benzyl, phenyl-($C_2$–$C_4$)alkyl, $C_1$–$C_4$ alkoxyi;
$R^{17}$ and $R^{16}$ are independently H or $C_1$–$C_4$ alkyl;
$R^7$ is H, $C_1$–$C_8$ alkyl, phenyl, halogen, or $C_1$–$C_4$ alkoxy;
$R^{11}$ is H or $C_1$–$C_3$ alkyl; $R^{12}$ is H or CH3;
A is selected from the group:
$C_1$–$C_7$ alkyl,

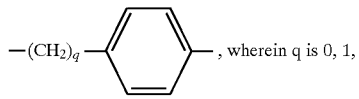, wherein q is 0, 1,

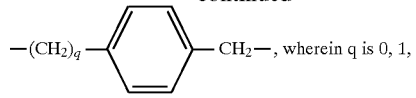$CH_2$—, wherein q is 0, 1,

—$(CH_2)_mS(CH_2)_2$—, wherein m = 1, 2,

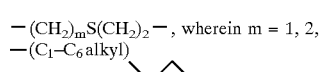 NC(=NH)$NH_2$, wherein v is 0–3 and provided that w=0,
—$(CH_2)_m$—O—($C_1$–$C_4$ alkyl)—NH—($C_1$–$C_6$ alkyl), wherein m=1–2,
$R^3$ and A may be taken together to form

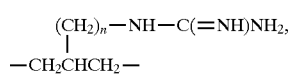

wherein n=0–1 and provided that w=0;
$R^9$ is H, $C_1$–$C_3$ alkyl;
$R^5$ is H, $C_1$–$C_3$ alkyl.

In the most preferred embodiment, the above-described process provides compounds of formula (I) wherein:
Z=benzyl;
Y=tosyl;
G=CBz;
$R^5$, $R^9$, $R^{16}$, $R^{17}$ and $R^{18}$ are H;
$R^{11}$ $R^{12}$, and $R^{14}$ are H or $CH_3$;
$R^{15}$ is H, $C_1$–$C_4$ alkyl, phenyl, benzyl, or phenyl-($C_2$–$C_4$) alkyl; and
$R^3$ is H or $C_1$–$C_3$ alkyl.

The above described process specifically provides a compound of formula:
w is 1;
p is 0;
$R^{19}$ is

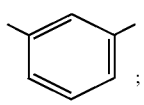;

$R^5$, $R^9$, $R^{17}$, $R^{15}$, $R^{11}$, $R^{12}$ are H;
$R^2$ is $C_2H_5$;
$R^3$ is $CH_3$; and
A is —$(CH_2)_3$—.

This invention also provides a process for the preparation of an intermediate compound of formula:

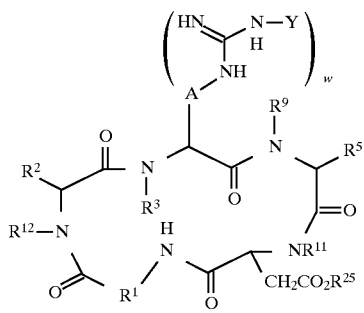

Formula (II)

comprising cyclizing a compound of formula:

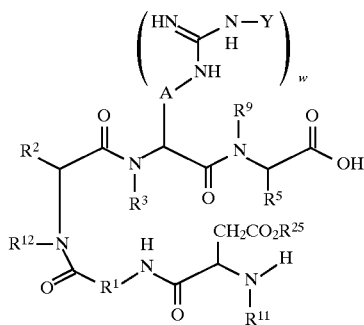

wherein:
T is Tos;
$R^1$ is

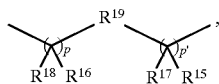

wherein:
and p' are 0 or 1;
$R^{19}$ is a $C_6$–$C_{14}$ saturated, partially saturated, or aromatic carbocyclic ring system or heterocyclic ring system composed of at least 1–3 heteroatoms selected from N, O, S; all these ring systems may be optionally substituted with 0–2 $R^7$;
$R^{17}$ and $R^{16}$ are independently selected from the group: hydrogen;
$C_1$–$C_4$ alkyl, optionally substituted with halogen;
$C_1$–$C_2$ alkoxy;
benzyl;
$R^{15}$ and $R^{18}$ are independently selected from the group: hydrogen,
$C_1$–$C_8$ alkyl substituted with 0–2 $R^8$,
$C_2$–$C_8$ alkenyl substituted with 0–2 $R^8$,
$C_2$–$C_8$ alknyl substituted with 0–2 $R^8$,
$C_3$–$C_8$ cycloalkyl substituted with 0–2 $R^8$,
$C_6$–$C_{10}$ bicycloalkyl substituted with 0–2 $R^8$, aryl substituted with 0–2 $R^{13}$,
a heterocylic ring system composed of 5–10 atoms including 1–3 nitrogen, oxygen, or sulfur heteroatoms, optionally substituted with 0–2 $R^{13}$;
$R^{15}$ and $R^{17}$ can alternatively join to form a 5–7 membered carbocyclic ring substituted with 0–2 $R^{13}$;
$R^{18}$ and $R^{16}$ can alternatively join to form a 5–7 membered carbocyclic ring substituted with 0–2 $R^{13}$;
$R^{15}$ and $R^{11}$ can alternatively join to form a 5–8 membered carbocyclic ring substituted with 0–2 $R^{13}$, when $R^{17}$ is H;

$R^7$ is independently selected at each occurrence from the group:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2R^{20}$, sulfonamide, formyl, $C_3$–$C_6$ cycloalkoxy, —OC(=O)$R^{20}$, —C(=O)$R^{20}$, —OC(=O)O$R^{20}$, —O$R^{20}$, —$CH_2OR^{20}$, $C_1$–$C_4$ alkyl optionally substituted with —$NR^2OR^{21}$;
$R^8$ is independently selected at each occurrence from the group:
=O, F, Cl, Br, I, —$CF_3$, —CN, —$CO_2R^{20}$, —C(=O)$NR^{20}R^{21}$, —$CH_2OR^{20}$, —OC(=O)R20, —$CH_2NR^{20}R^{21}$, —$NR^{20}R^{21}$;
$R^{13}$ is independently selected at each occurrence from the group:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2R^{20}$, sulfonamide, formyl, $C_3$–$C_6$ cycloalkoxy, —OC(=O)R20, —C(=O)R20, —OC(=O)O$R^{20}$, —O$R^{20}$, —$CH_2OR^{20}$, $C_1$–$C_4$ alkyl (substituted with —$NR^{20}R^{21}$);
$R^{20}$ is independently selected at each occurrence from the group:
H, $C_1$–$C_7$ alkyl, aryl, —($C_1$–$C_6$ alkyl)aryl, or $C_3$–$C_6$ alkoxyalkyl;
$R^{21}$ is independently selected at each occurrence from the group:
H, $C_1$–$C_4$ alkyl, or benzyl;
$R^{11}$ is H or $C_1$–$C_8$ alkyl;
$R^{12}$ is H or $C_1$–$C_8$ alkyl;
$R^{14}$ is H or $C_1$–$C_8$ alkyl;
$R^2$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, $(CH_2)_sNHC(=NH)(NH_2)$, $(CH_2)_sNHR^{21}$, wherein s=3–5;
$R^{12}$ and $R^2$ can be taken together to form —$(CH_2)_t$—, wherein t=2–4, or —$CH_2SC(CH_3)_2$—;
$R^3$ is H or $C_{1-C8}$ alkyl;
A is selected from the group:
—$C_1$–$C_7$ alkyl—,

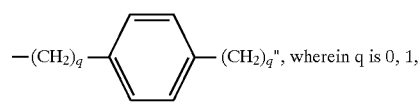, wherein q is 0, 1,

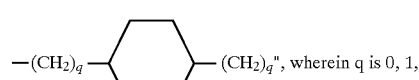, wherein q is 0, 1,

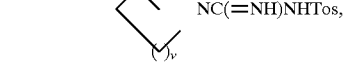

w wherein v is 0–3 and provide that w=0,

R³ and A may be taken together to form

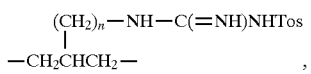

wherein n=0–1 and provided that w=0;
R⁹ is H, $C_1$–$C_8$ alkyl; and
R⁵ is H, $C_1$–$C_8$ alkyl.

In a preferred embodiment, the above described process provides an intermediate compound of formula (II) wherein:
R¹⁹ is selected from the following groups:

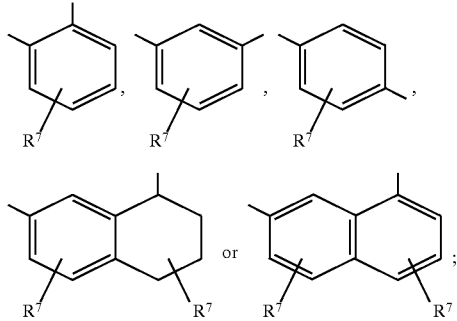

R¹⁵ and R¹⁸ are independently selected from H, $C_1$–$C_4$ alkyl, phenyl, benzyl, phenyl-($C_2$–$C_4$)alkyl, $C_1$–$C_4$ alkoxy;
R¹⁷ and R¹⁶ are independently H or $C_1$–$C_4$ alkyl;
R⁷ is H, $C_1$–$C_8$ alkyl, phenyl, halogen, or $C_1$–$C_4$ alkoxy;
R¹¹ is H or $C_1$–$C_3$ alkyl;
R¹² is H or $CH_3$;
A is selected from the group:

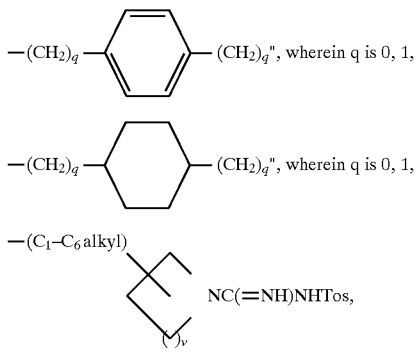

wherein v is 0–3 and provided that w=0,
R³ and A may be taken together to form

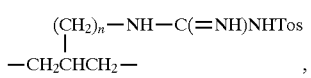

wherein n 0–1 and provided that w=0;
R⁹ is H, $C_1$–$C_3$ alkyl; and
R⁵ is H, $C_1$–$C_3$ alkyl.

In a more preferred embodiment, the above-described preferred process provides intermediate compounds of formula (II) wherein:
R⁵, R⁹, R¹⁶, R¹⁷ and R¹⁸ are H;
R¹¹, R¹², and R¹⁴ are H or $CH_3$;

R¹⁵ is H, $C_1$–$C_4$ alkyl, phenyl, benzyl, or phenyl-($C_2$–$C_4$) alkyl; and
R³ is H or $C_1$–$C_3$ alkyl.

The above-described process specifically provides intermediate compounds of formula (II) wherein:
w is 1;
p is 0;
R¹⁹ is

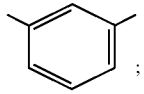

R⁵, R⁹, R¹⁷, R¹⁵, R¹¹, R¹², R¹⁴ are H;
R² is $C_2H_5$;
R³ is $CH_3$; and
A is —$(CH_2)_3$—.

This invention also provides intermediate compounds useful in the claimed processes for the preparation of compounds of formula (I). Said intermediate compounds have formulae:

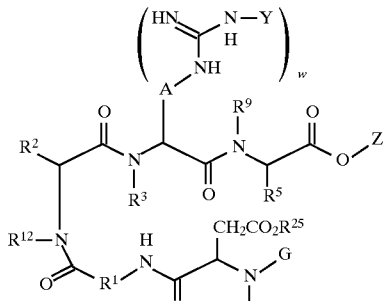

Formula III

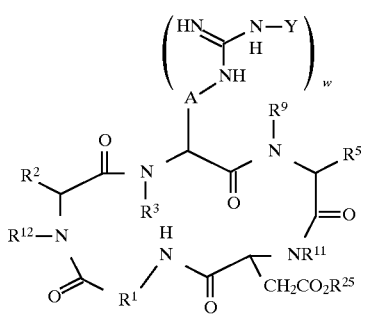

Formula IV wherein:
w=0 or 1;
Y is H or tosyl;
Z is H or benzyl;
G is H, CBZ;
R¹ is

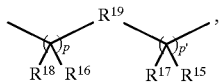

wherein:
p and p' are 0 or 1;
R¹⁹ is a $C_6$–$C_{14}$ saturated, partially saturated, or aromatic carbocyclic ring system or heterocyclic ring system composed of at least 1–3 heteroatoms selected from N, O, S; all these ring systems may be optionally substituted with 0–2 R⁷;

11

$R^{17}$ and $R^{16}$ are independently selected from the group:
hydrogen;
$C_1$–$C_4$ alkyl, optionally substituted with halogen;
$C_1$–$C_2$ alkoxy;
benzyl;
$R^{15}$ and $R^{18}$ are independently selected from the group:
hydrogen,
$C_1$–$C_8$ alkyl substituted with 0–2 $R^8$,
$C_2$–$C_8$ alkenyl substituted with 0–2 $R^8$,
$C_2$–$C_8$ alkynyl substituted with 0–2 $R^8$,
$C_3$–$C_8$ cycloalkyl substituted with 0–2 $R^8$,
$C_6$–$C_{10}$ bicycloalkyl substituted with 0–2 $R^8$,
aryl substituted with 0–2 $R^{13}$,
a heterocylic ring system composed of 5–10 atoms including 1–3 nitrogen, oxygen, or sulfur heteroatoms, optionally substituted with 0–2 $R^{13}$;
$R^{15}$ and $R^{17}$ can alternatively join to form a 5–7 membered carbocyclic ring substituted with 0–2 $R^{13}$;
$R^{18}$ and $R^{16}$ can alternatively join to form a 5–7 membered carbocyclic ring substituted with 0–2 $R^{13}$;
$R^{15}$ and $R^{11}$ can alternatively join to form a 5–8 membered carbocyclic ring substituted with 0–2 $R^{13}$, when $R^{17}$ is H;
$R^7$ is independently selected at each occurrence from the group:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2R^{20}$, sulfonamide, formyl, $C_3$–$C_6$ cycloalkoxy, —OC(=O)$R^{20}$, —C(=O)$R^{20}$, —OC(=O)O$R^{20}$, —O$R^{20}$, —$CH_2OR^{20}$, $C_1$–$C_4$ alkyl optionally substituted with —$NR^{20}R^{21}$;
$R^8$ is independently selected at each occurrence from the group:
=O, F, Cl, Br, I, —$CF_3$, —CN, —$CO_2R^{20}$, —C(=O)$NR^{20}R^{21}$, —$CH_2OR^{20}$, —OC(=O)R20, —$CH_2NR^{20}R^{21}$, —$NR^{20}R^{21}$;
$R^{13}$ is independently selected at each occurrence from the group:
phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2R^{20}$, sulfonamide, formyl, $C_3$–$C_6$ cycloalkoxy, —OC(=O)R20, —C(=O)R20, —OC(=O)O$R^{20}$, —O$R^{20}$, —$CH_2OR^{20}$, $C_1$–$C_4$ alkyl (substituted with —$NR^{20}R^{21}$);
$R^{20}$ is independently selected at each occurrence from the group:
H, $C_1$–$C_7$ alkyl, aryl, —($C_1$–$C_6$ alkyl)aryl, or $C_3$–$C_6$ alkoxyalkyl;
$R^{21}$ is independently selected at each occurrence from the group:
H, $C_1$–$C_4$ alkyl, or benzyl;
$R^{11}$ is H or $C_1$–$C_8$ alkyl;
$R^{12}$ is H or $C_1$–$C_8$ alkyli
$R^{14}$ is H or $C_1$–$C_8$ alkyl;
$R^2$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, $(CH_2)_s$NHC(=NH)(NH_2), $(CH_2)_sNHR^{21}$, wherein s=3–5;
$R^{12}$ and $R^2$ can be taken together to form —$(CH_2)_t$— wherein t=2–4, or —$CH_2SC(CH_3)_2$—;
$R^{14}$ and $R^2$ can be taken together to form —$(CH_2)_u$—, wherein u=2–5;

12

$R^3$ is H or $C_1$–$C_8$ alkyl;
A is selected from the group:
—$C_1$–$C_7$ alkyl-,

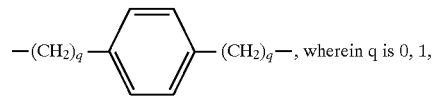

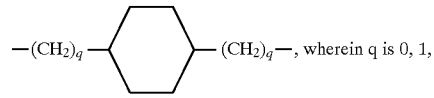

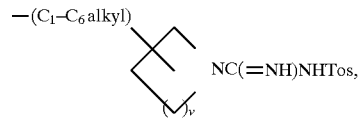

wherein v is 0–3 provided that and w=0,
—$(CH_2)_mO$—$(C_1$–$C_4$ alkyl)—, wherein m=1,2,
—$(CH_2)_mS$—$(C_1$–$C_4$ alkyl)—, wherein m=1,2;
$R^3$ and A may also be taken together to form

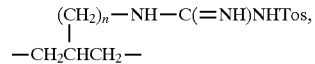

wherein n=0–1 and w=0;
$R^9$ is H, $C_1$–$C_8$ alkyl;
$R^5$ is H, $C_1$–$C_8$ alkyl; and
$R^{25}$ is t-butyl, $C_5$–$C_8$ cycloalkyl, or benzyl wherein the phenyl ring is substituted with 0–5 $C_1$–$C_4$ alkyl groups, $C_1$–$C_4$ alkoxy groups, or 1–2 halogen atoms.
Preferred intermediate compounds of formulae III and IV are those wherein:
Y is H or tosyl;
Z is H or benzyl;
G is H or CBZ;
$R^{19}$ is selected from:

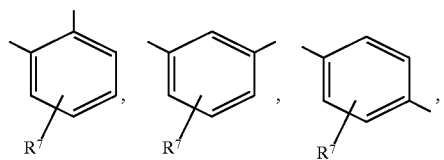

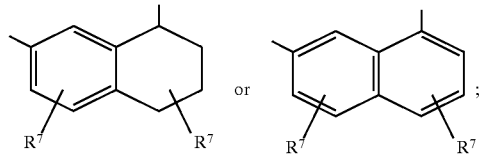

$R^{15}$ and $R^{18}$ are independently selected from H, $C_1$–$C_4$ alkyl, phenyl, benzyl, phenyl-($C_2$–$C_4$)alkyl, $C_1$–$C_4$ alkoxy;
$R^{17}$ and $R^{16}$ are independently H or $C_1$–$C_4$ alkyl;
$R^7$ is H, $C_1$–$C_8$ alkyl, phenyl, halogen, or $C_1$–$C_4$ alkoxy;
$R^{11}$ is H or $C_1$–$C_3$ alkyl;
$R^{12}$ is H or $CH_3$;
A is selected from the group:

—$C_1$–$C_7$ alkyl—,

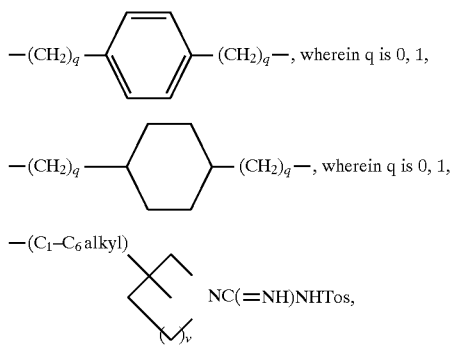

wherein v is 0–3 and provided that w=0,
$R^3$ and A may be taken together to form

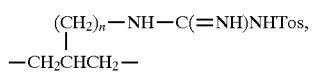

wherein n=0–1 and provided that w=0;
$R^9$ is H, $C_1$–$C_3$ alkyl; and
$R^5$ is H, $C_1$–$C_3$ alkyl.

Most preferred intermediate compounds of formulae III and IV are those preferred compounds wherein:

$R^5$, $R^9$, $R^{16}$, $R^{17}$ and $R^{18}$ are H;
$R^{11}$, $R^{12}$, and $R^{14}$ are H or $CH_3$;
$R^{15}$ is H, $C_1$–$C_4$ alkyl, phenyl, benzyl, or phenyl-($C_2$–$C_4$) alkyl; and
$R^3$ is H or $C_1$–$C_3$ alkyl.

Specifically preferred compounds of formulae II and IV are those wherein:

w is 1;
p is 0;
$R^{19}$ is

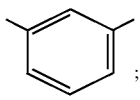

$R^5$, $R^9$, $R^{17}$, $R^{15}$, $R^{11}$, $R^{12}$, $R^{14}$ are H;
$R^2$ is $C_2H_5$;
$R^3$ is $CH_3$; and
A is —$(CH_2)_3$—.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. Two distinct isomers (cis and trans) of the peptide bond are known to occur; both can also be present in the compounds described herein, and all such stable isomers are contemplated in the present invention. Unless otherwise specifically noted, the L-isomer of the amino acid is the preferred stereomer of the present invention. The D and L-isomers of a particular amino acid are designated herein using the conventional 3-letter abbreviation of the amino acid, as indicated by the following examples: D-Leu, or L-Leu.

When any variable (for example, $R^1$ through $R^8$, m, n, p, X, Y, etc.) occurs more than one time in any constituent or in any formula, its definition on each occurrence is independent of its definition at every other occurrence. Also, combinations of substituents and/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like. "Halo" or "halogen" as used herein refers to fluoro, chloro, bromo and iodo; and "counterion" is used to represent a small, negatively charged species such as chloride, bromide, hydroxide, acetate, sulfate and the like.

As used herein. "aryl" is intended to mean phenyl or naphthyl; "carbocyclic" is intended to mean any stable 5- to 7- membered monocyclic or bicyclic or 7- to 14-membered bicyclic or tricyclic carbon ring, any of which may be saturated, partially unsaturated, or aromatic. Examples of such carbocyles include, but are not limited to cyclopentyl, cyclohexyl, phenyl, biphenyl, naphthyl, indanyl or tetrahydronaphthyl (tetralin).

As used herein, the term "heterocycle" or "heterocyclic ring system" is intended to mean a stable 5- to 7- membered monocyclic or bicyclic or 7- to 10-membered bicyclic heterocyclic ring which may be saturated, partially unsaturated, or aromatic, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrolinyl, tetrahydrofuranyl, tetrahydroquinolinyl, tetrahydroisoquinolinyl, decahydroquinolinyl or octahydroisoquinolinyl.

By "stable compound" or "stable structure" is meant herein a compound that is sufficiently robust to survive isolation to a useful degree of purity from a reaction mixture, and formulation into an efficacious therapeutic agent.

The term "substituted", as used herein, means that one or more hydrogen on the designated atom is replaced with a selection from the indicated group, provided that the designated atom's normal valency is not exceeded, and that the substitution results in a stable compound.

As used herein, the term "amine protecting group" means any group known in the art of organic synthesis for the protection of amine groups. Such amine protecting groups include those listed in Greene, "Protective Groups in Organic Synthesis" John Wiley & Sons, New York (1981) and "The Peptides: Analysis, Sythesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbor,yl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to: mineral or organic acid salts of basic residues such as amines; alkali or organic salts of acidic residues such as carboxylic acids; esters of carboxylates; acetate, formate and benzoate derivatives of alcohols and amines; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Reminaton's Pharmaceutical Sciences*, 17th ed., Mack Publishing Company, Easton, PA, 1985, p. 1418, the disclosure of which is hereby incorporated by reference.

The term "amino acid" as used herein means an organic compound containing both a basic amino group and an acidic carboxyl group. Included within this term are modified and unusual amino acids,such as those disclosed in, for example, Roberts and Vellaccio (1983) *The Peptides*, 5: 342 –429, the teaching of which is hereby incorporated by reference.

The term "amino acid residue" as used herein means that portion of an amino acid (as defined herein) that is present in a peptide or pseudopeptide. The term "peptide" as used herein means a linear compound that consists of two or more amino acids (as defined herein) that are linked by means of peptide or pseudopeptide bonds.

Synthesis

The following abbreviations are used herein:

| | |
|---|---|
| D-Abu | D-2-aminobutyric acid |
| β-Ala or bAla | 3-aminopropionic acid |
| Boc | t-butyloxycarbonyl |
| Boc-iodo-Mamb | t-butyloxycarbonyl-3-aminomethyl-4-iodo benzoic acid |
| Boc-Mamb | t-butyloxycarbonyl-3-aminomethylbenzoic acid |
| Boc-ON | [2-(tert-butyloxycarbonyloxylimino)-2-phenylacetonitrile |
| Cl$_2$Bzl | dichlorobenzyl |
| CBZ | Carbobenzyloxy |
| DCC | dicyclohexylcarbodiimide |
| DIEA | diisopropylethylamine |
| di-NMeOrn | N-αMe-N-γMe-ornithine |
| DMAP | 4-dimethylaminopyridine |
| HBTU | 2-(1H-Benzotriazol-1-yl)-1,1,3,3-tetramethyluronium hexafluorophosphate |
| NMeArg or MeArg | α-N-methyl arginine |
| NMeAmf | N-Methylaminomethylphenylalanine |
| NMeAsp | α-N-methyl aspartic acid |
| NMeGly or MeGly | N-methyl glycine |
| NMe-Mamb | N-methyl-3-aminomethylbenzoic acid |
| NMM | N-methylmorpholine |
| OcHex | O-cyclohexyl |
| OBzl | O-benzyl |
| TBTU | 2-(1H-Benzotriazol-1-yl)-1,1,3,3-tetramethyluronium tetrafluoroborate |
| Tos | tosyl |

The following conventional three-letter amino acid abbreviations are used herein; the conventional one-letter amino acid abbreviations are not used herein:

Ala=alanine

Arg=arginine

Asn=asparagine

Asp=aspartic acid

Cys=cysteine

Gln=glutamine

Glu=glutamic acid

Gly=glycine

His=histidine

Ile=isoleucine

Leu=leucine

Lys=lysine

Met=methionine

Nle=norleucine

Orn=ornithine

Phe=phenylalanine

Phg=phenylglycine

Pro=proline

Ser=serine

Thr=threonine

Trp=tryptophan

Tyr=tyrosine

Val=valine

The present invention provides a short process for the synthesis of compounds of formula (I). The provided process is accomplished using commercial available materials. The overall process is novel: it utilizes novel reaction steps, novel reaction sequences, and novel reaction intermediates. In practicing the rovided invention, knowledge of a number of standard techniques known to those in the art is required. The following discussion and references are offered to provide such knowledge.

Generally, peptides are elongated by deprotecting the α-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, according to the method originally described by Merrifield, J. Am. Chem. Soc., 85, 2149–2154 (1963), "The Peptides: Analysis, Synthesis, Biology, Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Sythesis" Springer-Verlag, New York (1984), the disclosures of which are hereby incorporated by reference.

The coupling of two amino acid derivatives, an amino acid and a peptide, two peptide fragments, or the cyclization of a peptide can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP—Cl, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids must be protected during the coupling reactions to avoid undesired bond formation. The protecting groups that can be used, methods of using them to protect amino acids, and methods to remove them are listed in Greene, "Protective Groups in Organic Synthesis" John Wiley & Sons, New York (1981) and "The Peptides: Analysis, Sythesis, Biology, Vol. 3, Academic Press, New York (1981), the disclosure of which is hereby incorporated by reference.

The α-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) *J. Org. Chem.* 45, 1295–1300) chloro or bromomethyl resin, hydroxymethyl resin, and aminomethyl resin. Many of these resins are commercially available with the desired C-terminal amino acid already incorporated.

The α-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert- butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred α-amino protecting group is either Cbz, Boc or Fmoc. Many amino acid derivatives suitably protected for peptide synthesis are commercially available.

The α-amino protecting group is cleaved prior to the coupling of the next amino acid. When the Cbz group is used, the reagents of choice are hydrogenation conditions using hydrogen at atmospheric pressure or in a Parr apparatus at elevated hydrogen pressure, or cyclohexene or ammonium formate over palladium, palladium hydroxide on charcoal or platinum oxide in methanol, ethanol or tetrahydrofuran, or combination of these solvents (P. N. Rylander, Hydrogenation Methods, Acedemic Press, 1985). When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

Any of the amino acids bearing side chain functionalities must be protected during the preparation of the peptide using any of the above-identified groups. Those skilled in the art will appreciate that the selection and use of appropriate protecting groups for these side chain functionalities will depend upon the amino acid and presence of other protecting groups in the peptide. The selection of such a protecting group is important in that it must not be removed during the deprotection and coupling of the α-amino group.

For example, when Cbz is chosen for the α-amine protection the following protecting groups are acceptable: p-toluenesulfonyl (tosyl) moieties for arginine; t-butyloxycarbonyl, phthalyl, or tosyl for lysine or ornithine; alkyl esters such as cyclopentyl for glutamic and aspartic acids; alkyl ethers for serine and threonine; and the indole of tryptophan can either be left unprotected or protected with a formyl group.

When Boc is chosen for the α-amine protection the following protecting groups are acceptable: p-toluenesulfonyl (tosyl) moieties and nitro for arginine; benzyloxycarbonyl, substituted benzyloxycarbonyls, or tosyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the α-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation and cyclization of the peptide is completed all of the protecting groups are removed. For the liquid phase synthesis the protecting groups are removed in the manner dictated by the choice of protecting groups. These procedures are well known to those skilled in the art. Unusual amino acids used in this invention can be synthesized by standard methods familiar to those skilled in the art ("The Peptides: Analysis, Sythesis, Biology, Vol. 5, pp. 342–449, Academic Press, New York (1981)). N-Alkyl amino acids can be prepared using proceedures described in previously (Cheung et al., (1977) *Can. J. Chem.* 55, 906; Freidinger et all, (1982) *J. Org. Chem.* 48, 77 (1982)), which are incorporated here by reference.

The process of the present invention utilizes the general methods described above along with the novel methods described below to prepare the compounds of Formula (I).

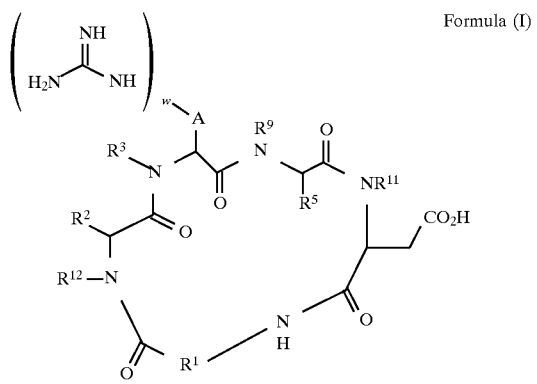

Formula (I)

The process of the present invention begins with the sequence of steps shown in Scheme 1.

In Step 1, the dipeptide 3 is prepared by coupling amino acid 1 with an appropriately substituted carboxy protected amino acid 2. Step 1 utilizes any of the previously described amide bond forming reactions. The preferred method of Step 1 for the preparation of the compound of formula 3 wherein Z is benzyl, X is Boc and Y is tosyl is via reaction of the corresponding carboxylic acid of formula 1 with glycine benzyl ester, in the presence of the HBTU in the solvent THF, with diisopropy ethylamine as the acid scavenger, at ambient temperature.

In Step 2, the N-α-alkyl dipeptide 4 is prepared by deprotection of the corresponding compound of formula 3 using the appropriate conditions for removal of the selected protecting group, as shown in Scheme 1. For example, for compounds of formula 3 wherein X is Boc, one may use any of the many deprotection methods well known in the literature, (see: M. Bodanszky and A. Bodanszky, The Practice of Peptide Synthesis, Springer-Verlag). The preferred method for the preparation of compound 4 wherein Z is benzyl, involves acid treatment of compound 3 wherein X is Boc with TFA. Alternatively, the reaction may be carried out with HCl or sulfuric acid in a solvent, such as ethyl acetate.

Step 3 of the process involves preparation of tripeptide 6 by coupling of an appropriately substituted N-α protected amino acid compound of formula 5 with the N-α-alkyl dipeptide compound 4. Compounds of formula 5 are commercially available (Sigma, BOCHEM). Step 3 may be Scheme 1

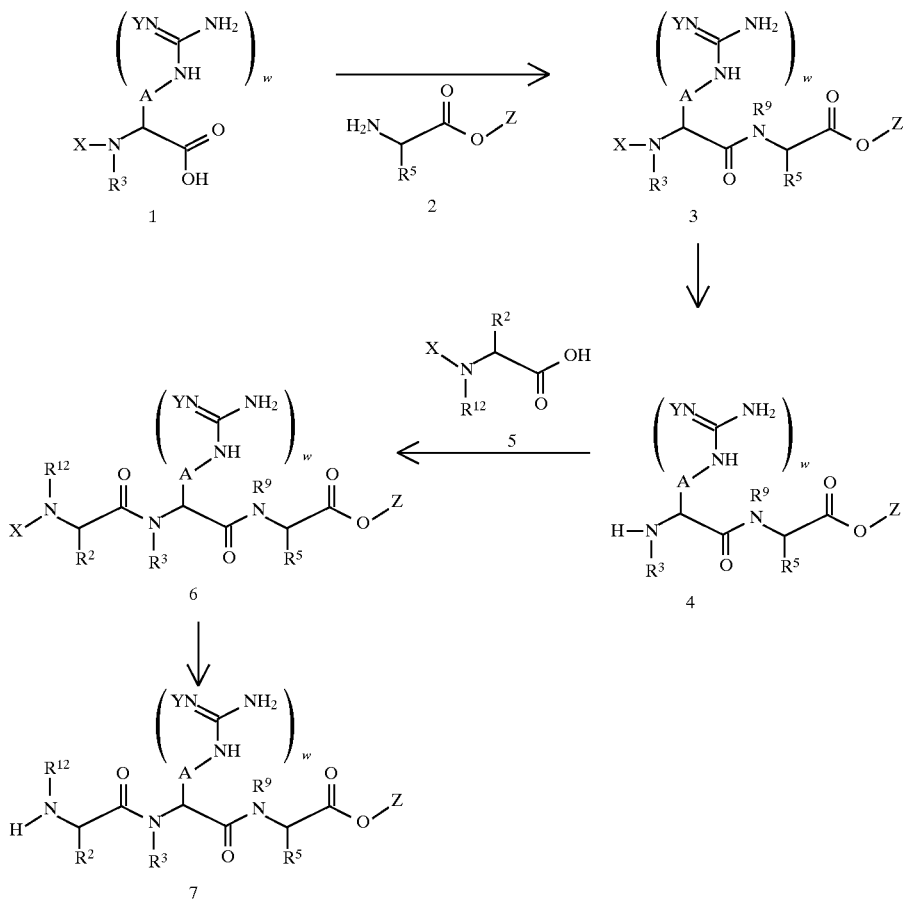

accomplished using any of the previously described methods for forming amide bonds. For Step 3, the preferred method to prepare compound 6 wherein X is Boc, $R^3$ is alkyl, and Z is benzyl, is to activate the N-α-Boc protected amino acid of the corresponding compound of formula 5 with HBTU or a carbodiimide and 1-hydroxybenzotriazole in the presence of a compound of formula 4 wherein $R^3$ is alkyl Z is benzyl, and Y is a protecting group, in acetonitrile, at ambient temperature.

In Step 4, compound 7 is prepared by acidic deprotection of the N-α-Boc-protected tripeptide, 6, using conditions outlined above. The preferred deprotection methods for preparation of a compound of formula 7 wherein Z is benzyl from compound 6 wherein X is Boc, include: reaction with TFA or $HCl$ in an solvent such as ethyl acetate, over a temperature range between ambient temperature and 40° C.

Steps 5–8 of the process of this invention are shown in Scheme 2. In Step 5, the fully elaborated protected linear peptide compound, 9, is prepared by coupling the carboxylic acid compound, 8, and the amino tripeptide compound, 7. This step may be carried out using any of the previously described methods for forming amide bonds. The preferred coupling method for the preparation of the linear pentapeptide compound of formula 9 wherein Z is benzyl and G is Cbz, from the amino compound 7 wherein Z is benzyl and the carboxylic acid compound of formula 8 wherein G is Cbz, utilizes HBTU, diisopropyl ethylamine in acetonitrile at ambient temperature. Other coupling reagents, such as 1-(3-dimethylaminopropyl)-3-ethylcarbodiimide hydrochloride or O-benzotriazol-1-yl-N,N,N',N'-tetramethylurion hexafluorophosphate carbonyldiimiazole, hydroxysuccinate

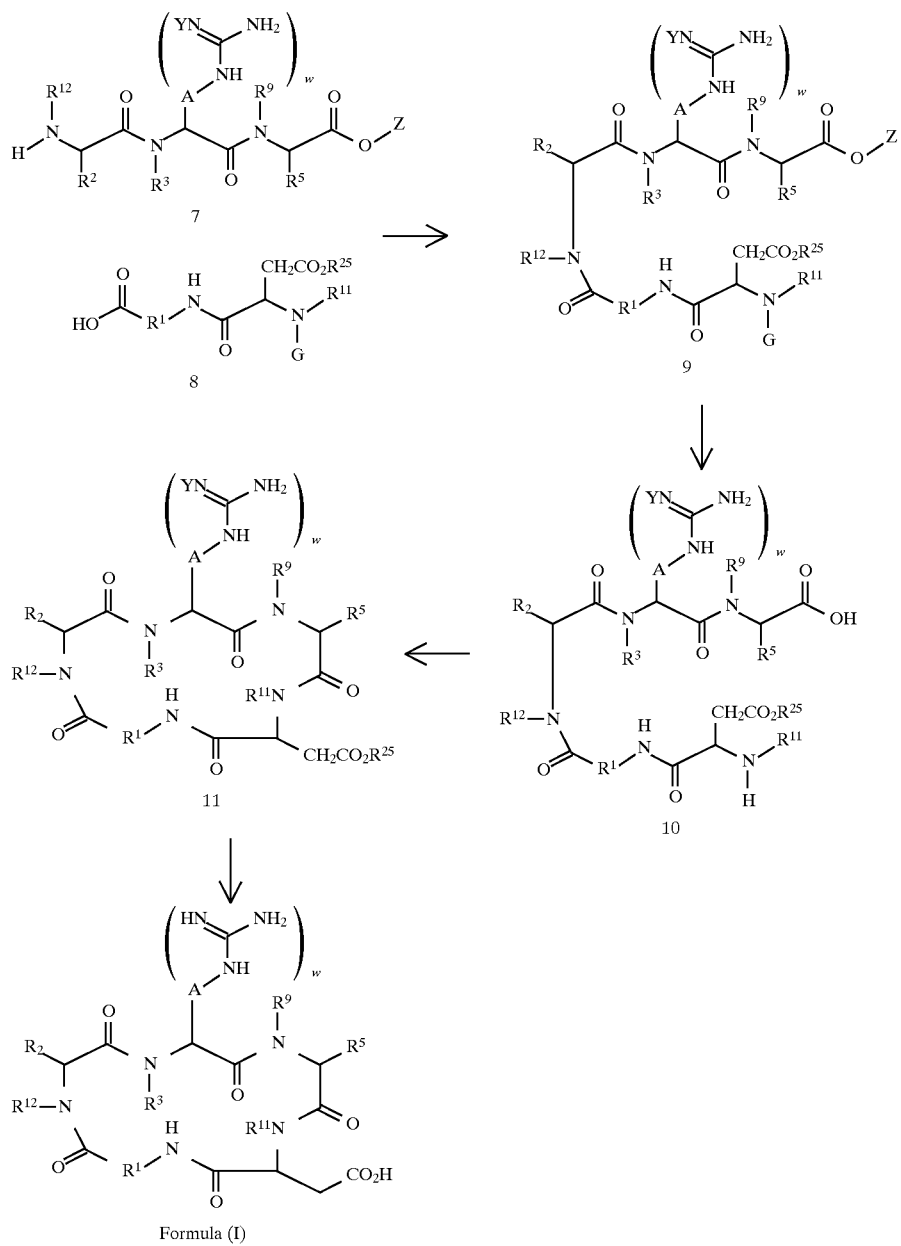

Scheme 2 ester or isobutylchloroformate and 1-hydroxybentriazole with N-methylmorpholine, may also give similar results.

In Step 6, the free amino acid peptide compound, 10, is prepared by the deprotection of compound 9. For example, deprotection of 9 wherein Z is benzyl and G is Cbz may be accomplished using any of a variety of methods well known in the literature for the deprotection of benzyl and Cbz groups. Such methods include: reaction with 5–10% palladium on charcoal and ammonium formate or cyclohexene, in an alcohol solvent, over a temperature range between ambient temperature and 70° C., or 5–10% palladium on charcoal in an alcohol solvent under 1 atm or elvated hydrogen pressure. The preferred method, to prepare the free amino acid compound, 10, by deprotection of compound 9 wherein G is Cbz and Z is benzyl is via reaction with 10% palladium on charcoal in methanol under 5 atm hydrogen pressure at ambient temperature.

In Step 7, the cyclic compound, 11, is prepared by cyclization of the linear peptide, 10. This step may be accomplished using any of the previously described amide bond forming reactions. The preferred cyclization method for the preparation of compounds of formula 11 from the linear compound, 10, utilizes HBTU and disiopropyl ethylamine in a solvent such as acetonitrile at ambient temperature. Other coupling reagents such as 1-(3-dimethylaminopropyl)-3-ethylcarbodiimide hydrochloride, dicyclohexylcarbodiimide, or O-benzotriazol-1-yl-N,N,N',N'-tetramethylurion hexafluorophosphate and 1-hydroxybentriazole with N-methylmorpholine may also applicable in this step.

In Step 8, compounds of Formula (I) are prepared by reaction of the corresponding compound of formula 11 to remove the utilized protecting groups. Where the protecting groups are t-butyl and tosyl, the compound of formula 11 is first reacted with TFA to remove the t-butyl protecting group, and then with triflic acid and anisole to remove the tosyl group at a temperature range of −40° C. to −6° C.

Scheme 3

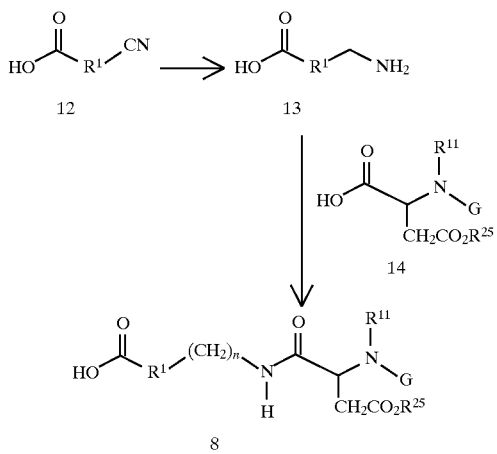

The preparation of intermediate compound 8 is shown in Scheme 3. The pseudodipeptide 8 is prepared by coupling the amino carboxylic acid compound of formula 13 with the activated carboxylic acid of an appropriately substituted N-α protected amino acid of formula 14 wherein G is a protecting group such as Cbz, using any of the amide bond forming reactions previously described. The preferred method for preparing the carboxylic acid compound, 8, wherein $R^1$ is phenyl, is by reaction of the salt form of the free amino acid compound, 13 wherein $R^1$ is phenyl, with a carboxylic acid, 14, activated with N,N'-carbonyldiimidazole, in the solvent N,N-dimethylformamide, at ambient temperature. Alternatively, the carboxylic acid can be activated as the N-hyroxysuccinate ester in a solvent such as methylene chloride or N,N-dimethylformamide.

The amino carboxylic acid compound of formula 13 can be purchased or can be prepared by reduction of the appropriately substituted cyano carboxylic acid compound (12) by methods well known in the literature for reducing cyano groups, as described in Tetra. Lett., 4393 (1975); Modern Synthetic Reactions, H.O. House (1972); or Harting et al. J. Am. Chem. Soc., 50: 3370 (1928). Other analogues of compounds of formula 13 may be prepared by any of a number of methods well known in the literature, for example, Olsen, J. Org. Chem. (1970) 35: 1912).

Examples

All chemicals and solvents (reagent grade) were used as supplied from the vendors cited without further purification. t-Butyloxycarbonyl (Boc) amino acids and other starting amino acids may be obtained commercially from Bachem Inc., Bachem Biosciences Inc. (Philadelphia, Pa.), Advanced ChemTech (Louisville, Ky.), Peninsula Laboratories (Belmont, Calif.), or Sigma (St. Louis, Mo.). 2-(lH-Benzotriazol-1-yl)-l,1,3,3-tetramethyluronium hexafluorophosphate (HBTU) and TBTU were purchased from Advanced ChemTech. N-methylmorpholine (NMM), m-cresol, D-2-aminobutyric acid (Abu), trimethylacetylchloride, diisopropylethylamine (DIEA), 3-cyanobenzoic acid and [2-(tert-butyloxycarbonyloxylimino)-phenylacetonitrile] (Boc-ON) were purchased from Aldrich Chemical Company. Dimethylformamide (DMF), ethyl acetate, chloroform ($CHCl_3$), methanol (MeOH), pyridine and hydrochloric acid (HCl) were obtained from Baker. Acetonitrile, dichloromethane (DCM), acetic acid (HOAc), trifluoroacetic acid (TFA), triflic acid, anisole ethyl ether, triethylamine, acetone, and magnesium sulfate were purchased from EM Science. Palladium on carbon catalyst (10% Pd) was purchased from Aldrich Chemical Company or Fluka Chemical Company. Absolute ethanol was obtained from Quantum Chemical Corporation. Thin layer chromatography (TLC) was performed on Silica Gel 60 $F_{254}$ TLC plates (layer thickness 0.2 mm) which were purchased from EM Separations. TLC visualization was accomplished using UV light, iodine, and/or ninhydrin spray. Melting points were determined using a Thomas Hoover or Electrothermal 9200 melting point apparatus and are uncorrected. NMR spectra were recorded on a 300 MHz General Electric QE-300, Varian 300, or Varian 400 spectrometer. Fast atom bombardment mass spectrometry (FAB-MS) was performed on a VG Zab-E double-focusing mass spectrometer using a Xenon FAB gun as the ion source or a Finnigan MAT 8230.

EXAMPLE 1

Step 1: Carbobenzyloxy-aspartic acid (t-butyl)-m-aminomethylbenzoic acid

A 4-necked round bottom flask (250 mL) equipped with a magnetic stirrer, thermometer and a condenser with nitrogen gas-inlet tube and a bubbler was purged with nitrogen for 10 min. This flask was charged with N-carbobenzyloxy-β-t-butyl aspartate (15.0 g, 0.05 mol), 1,1-carbonyldiimidazole (8.3 g, 0.05 mol) and DMF (70 mL). The mixture which resulted was stirred at room temperature for 1 h, and m-aminomethylbenzoic sodium salt (7.8 g, 0.05 mol) was added in one portion. This mixture was stirred at room temperature for 24 h. Ethyl acetate (900 mL) was added, and the organic layer was washed with aqueous citric acid (5%, 2×150 mL), water (2×150 mL), brine (2×150 mL) and dried (MgSO$_4$). The solvent was removed under reduced pressure and the residue was crystallized from the mixed solvent of ethyl acetate and hexane to provide the desired product (16.6 g, 73% yield). MS (FAB) m/e 457.3 (M+1).

Step 2. t-Butyloxycarbonyl-N-methylarginine(tosyl)-glycinebenzyl ester

A 4-necked round bottom flask (500 mL) equipped with a mechanical stirrer, thermometer and a condenser with nitrogen gas-inlet tube and a bubbler was purged with nitrogen for 10 min. This flask was charged with t-butyloxycarbonyl-N-methylargine (tosyl) (45.0 g, 0.10 mol), glycine benzyl ester p-toluenesulfonic acid salt (41.2 g, 0.12 mol), O-benzotriazole N, N, N, N-tetramethyluronium hexafluorophosphate (HBTU) (39.0 g, 0.1 mol) and THF (100 mL). The mixture which resulted was cooled in an ice-water bath (5° C.), and the diisopropyl ethylamine (33.4 g, 45 mL) was added dropwise over a 5 min period. The ice-water bath was removed and the solution was stirred at room temperature (~22° C.) for 6.5 h. To the reaction mixture ethyl acetate (600 mL) was added, and the organic layer was washed with aqueous citric acid (5%, 3×250 mL), water (300 mL), brine (3×300 mL) and dried (MgSO$_4$, 40 g). The solvent was removed under reduced pressure, and the residue was dried under vacuum to provide the desired product t-butyloxycarbonyl-N-methylarginine (tosyl)-glycinebenzyl ester (84.4 g, 100% yield). MS(FAB) m/e 590.3 (M+1).

Step 3. N-methylarginine(tosyl)glycinebenzyl ester

The t-Butyloxycarbonyl-N-methylarginine(tosyl) glycinebenzyl ester (84.3 g) was dissolved in trifluoroacetic acid (250 mL) at 33° C. The solution was stirred at same temperature for 30 min and the trifluoroacetic acid was removed under reduced pressure at the temperature range between 40–50° C. The residue (176.2 g) was dissolved in ehtyl acetate (3 L), and the organic layer was washed with brine (2×350 mL). To this organic layer aqueous sodium bicarbonate (saturated, 900 mL) was added, and the pH of the mixture was adjusted to 7.02. The layers were separated and the organic layer was dried (MgSO$_4$). The solvent was removed under reduced pressure to give the disired product N-methylarginine(tosyl)glycinebenzyl ester (71.5 g, 100%). MS (FAB) m/e 490.1 (M+1, free base).

Step 4. t-Butyloxycarbonyl-D-α-aminobutyric acid-N-methylarginine(tosyl)-glycinebenzyl ester A 4-necked round bottom flask (500 mL) equipped with a mechanical stirrer, thermometer and a condenser with nitrogen gas-inlet tube and a bubbler was purged with nitrogen for 10 min. This flask was charged with N-methylarginine(tosyl)-glycinebenzyl ester of Step 3 (70.4 g), t-butyloxycarbonyl-D-α-aminobutyric acid dicyclohexylamine salt (44.0 g, 0.11 mol), HBTU (45.0 g, 0.18 mol) and acetonitrile (180 mL). The solution which resulted was cooled to 5° C. in an ice-water bath. To this solution disiopropyl ethyl amine (30.0 g) was added dropwise over a 10 min period. The solution wahich resulted was stirred at room temperature for 22 h, and ethylacetate (1 L) was added. The organic layer was washed with aqueous citric acid (5%, 3×240 mL), water (360 mL), saturated sodium bicarbonate (360 mL) and brine (360 mL). The organic layer was dried (MgSO$_4$), and the solvent was removed under reduced pressure, and further dried under vacuum to provide the desired product (120.3 g, 100%). MS(FAB) m/e 675.1 (M+1).

Step 5. D-α-aminobutyric acid-N-methylarginine(tosyl)-glycinebenzyl ester

The D-α-aminobutyric acid-N-methylarginine(tosyl)-glycinebenzyl ester (118.1 g) was dissolved in trifluoroacetic acid (200 mL) at 33° C. The solution was stirred at same temperature for 30 min and the trifluoroacetic acid was removed under reduced pressure at the temperature range between 40–50° C. The residue (234.4 g) was dissolved in ehtyl acetate (3 L), and the organic layer was washed with brine (2×800 mL). To this organic layer aqueous sodium bicarbonate (saturated) was added, and the pH of the mixture was adjusted to 7.00. The layers were separated and the organic layer was dried (MgSO$_4$, 200 g). The solvent was removed under reduced pressure, and the residue was dried under vacuum to give the disired product (94.24 g, 100%). MS(FAB) m/e 575.1 (M+1, free base).

Step 6. Carbobenzyloxy-aspartic acid (t-butyl)-m-aminomethylbenzoic acid- -aminobutyric acid-N-methylarginine-(tosyl)-glycinebenzyl ester A 4-necked round bottom flask (1.0 L) equipped with a mechanical stirrer, thermometer and a condenser with nitrogen gas-inlet tube and a bubbler was purged with nitrogen for 10 min. This flask was charged with D-α-aminobutyric acid-N-methylarginine(tosyl)-glycinebenzyl ester of Step 5 (93.2 g), Carbobenzyloxy-aspartic acid (t-butyl)-m-aminomethylbenzoic acid of Step 1 (46.0 g, 0.1 mol) HBTU (40.0 g, 0.11 mol) and acetonitrile (500 mL). The solution which resulted was cooled to 50° C. in an ice-water bath. To this solution diisopropyl ethyl amine (40.0 g, 0.31 mol) was added dropwise over a 10 min period. The solution wahich resulted was stirred at room temperature for 2 h, and ethylacetate (2.5 L) was added. The organic layer was washed with aqueous citric acid (5%, 2×1.0 L), saturated sodium bicarbonate (2×550 mL) and brine (2×300 mL). The organic layer was dried (MgSO$_4$, 150 g), and the solvent was removed under reduced pressure. The residue was further dried under vacuum to provide the desired product (142.6 g, 100%). MS(FAB) m/e 1013.3 (M$^+$).

Step 7. Aspartic acid (t-butyl)-m-aminomethylbenzoic acid-aminobutyric acid-N-methylarginine-(tosyl)-glycine To the solution of Carbobenzyloxy-aspartic acid (t-butyl)-m-aminomethylbenzoic acid- -aminobutyric acid-N-methylarginine-(tosyl)-glycinebenzyl ester (141.1 g) in methanol (1.2 L), was added Pd/C (10%, 22.0 g) in small portions. The debenzylation was carried out under hydrogen pressure of 5 Psi for 2.5 h. The reaction mixtutr was filtered through celite, and the filter cake was washed with methanol (2×200 mL). The solvent was removed under reduced pressure to provide the desire product (110.3 g, 100%). MS(FAB) m/e 789.4 (M+1).

Step 8. Cyclo-D-α-aminobutyric acid-N-methylarginine (tosyl)-glycine-aspartic acid (t-butylester)-m-aminomethylbenzoic acid A 4-necked round bottom flask (2.0 L) equipped with a mechanical stirrer, thermometer and a condenser with nitrogen gas-inlet tube and a bubbler was purged with nitrogen for 10 min. This flask was charged with HBTU (26.5 g, 0.07 mol) and acetonitrile (400 mL)). The solution of aspartic acid (t-butyl)-m-aminomethylbenzoic acid- -aminobutyric acid-N-methylarginine-(tosyl)-glycine from Step 7 (44.0 g) and diisopropyl ethyl amine (11.8 g, 0.09 mol) in mixed solvent of DMF (88 mL) and acetopnitrile (400 mL) was added dropwise over a 3 h period. The reaction mixture was kept stirring for 2 h after the completion of the additiopn. The product was precipitated out from the reaction media, and collected by a filtration (10.5 g). The solvent was removed under reduced pressure, and the residue was dissolved in ethyl acetate (550 mL). This ethyl acetate layer was washed with aqueous sodium bicarbonate (saturated, 2×200 mL) and brine (2×200 mL). The organic layer was dried (MgSO$_4$, 40 g), and the solvent was removed under reduced pressure. The residue was crystallized from acetonitrile to give the desired product (11.5 g). This cyclization step provided the desired product (22.0 g) in 51% yield. MS(FAB) m/e 771.2 (M+1).

Step 9. Cyclo-D-α-aminobutyric acid-N-methylarginine-glycine-aspartic acid m-aminomethylbenzoic acid.

A 4-necked round bottom flask (1.0 L) equipped with a mechanical stirrer, thermometer and a dropping funnel with nitrogen gas-inlet tube and a bubbler was purged with nitrogen for 30 min. This flask was cooled in an ice-water bath, and charged with the compounds of Step 8 (13.5 g, 0.02 mol) and trifluoroacetic acid (68 mL). The ice-water bath was removed, and the mixture which resulted was stirred at room temperaure (~20° C.) for 20 min. The solution was cooled to −18° C., and triflic acid (68 mL) was added dropwise between the temperature range of −18 to −100C. After addition, the reaction mixture was cooled to −30° C., and anisole (13.5 mL) was added at the temperature range between −30 to −10° C. The reaction mixture was stirred at the temperature range between −14 to −8° C. for 1 h, and then cooled to −30° C. To this solution, butyl ether (400 mL) was added at the temperature range between −30 to −8° C. in 30 min. The stirring was stopped and the mixture which resulted was kept at −30° C. for 30 min. The product was collected by a filtration, and the filter cake was washed by butyl ether (2×100 mL). This filter cake was dissolved in a mixed solvent of acetone and water (1/1, 200 mL), and the solution which resulted was filtered (#54 filter paper). The pH of the filtration was adjusted to 4.65–4.95 by adding AG-1-X8 resin (164 g) and kept stirring for 1 h. The mixture was filtered and the filter cake was washed with a mixed solvent of acetone and water (1/1, 2×50 mL). The solvent was removed under reduced pressure and the residue was washed with isopropanol (40 ml and 2×10 mL) and collected by a filtration. The product was dried under nitrogen in a vacuum oven at 25° C. for 18 h to provide the desired product (I) (10.9 g, 100%). MS(FAB) m/e 561.3 (M+1). The product is a compound of formula (I) wherein:

w is 1;
p is 0;
$R^{19}$ is

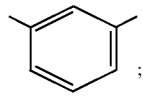;

$R^5$, $R^9$, $R^{17}$, $R^{15}$, $R^{11}$, $R^{12}$, $R^{14}$ are H;
$R^2$ is $C_2H_5$;
$R^3$ is $CH_3$; and
A is —$(CH_2)_3$—.

What is claimed is:

1. A process for the preparation of a compound of formula:

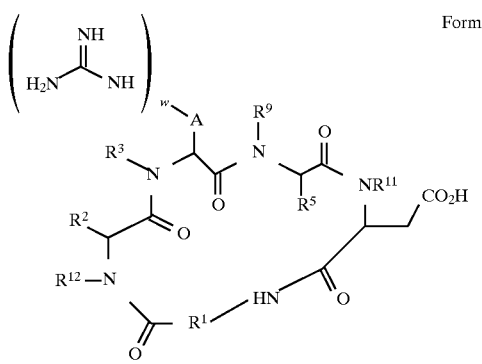

Formula (I)

comprising the steps of:

(a) coupling an amino tripeptide of formula:

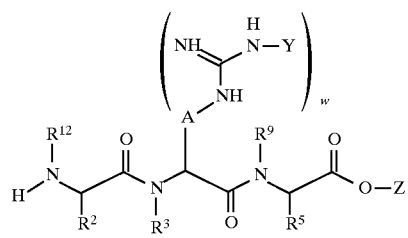

wherein z is a carboxylic acid protecting group and Y is an amine protecting group, with a carboxylic acid derivative of formula:

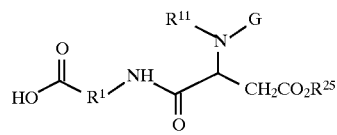

wherein G is an amine protecting group, to produce a protected linear peptide of formula:

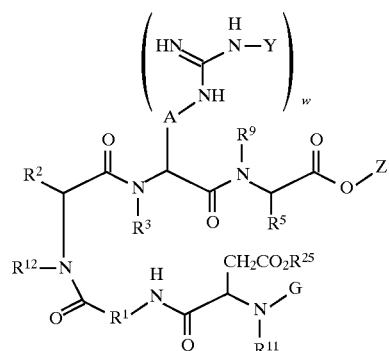

(b) removing the Z and G protecting groups of the product of Step (a) in one step to produce a deprotected linear peptide of formula:

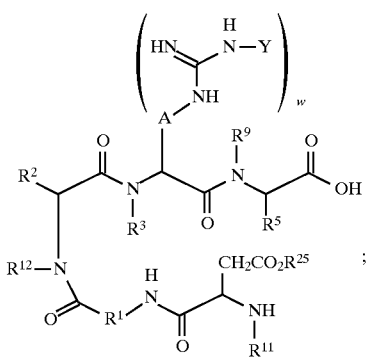

(c) cyclizing the deprotected linear peptide of Step (b) to produce a cyclic peptide of formula:

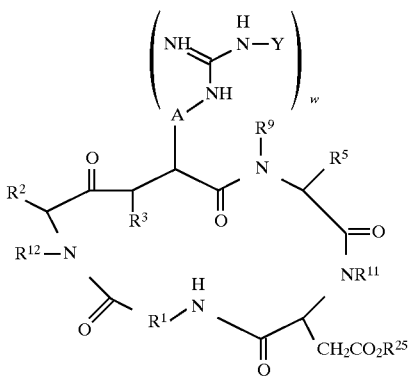

(d) removing the Y group and $R^{25}$ of the product of Step (c) to produce an amine of formula (I):

wherein:

w is 0 or 1;

$R^1$ is

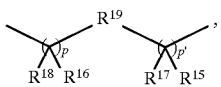

wherein p and p' are 0 or 1;

$R^{19}$ is a $C_6-C_{14}$ saturated, partially saturated, or aromatic carbocyclic ring system or heterocyclic ring system composed of at least 1–3 heteroatoms selected from the group consisting of N, O, and S; all these ring systems may be optionally substituted with 0–2 $R^7$;

$R^{17}$ and $R^{16}$ are independently selected form the group consisting of:
hydrogen;
$C_1-C_4$ alkyl, optionally substituted with halogen;
$C_1-C_2$ alkoxy; and
benzyl;

$R^{15}$ and $R^{18}$ are independently selected form the group consisting of;
hydrogen, $C_{1-4}$ alkoxy
$C_1-C_8$ alkyl substituted with 0–2 $R^8$,
$C_2-C_8$ alkenyl substituted with 0–2 $R^8$,
$C_2-C_8$ alkynyl substituted with 0–2 $R^8$,
$C_3-C_8$ cycloalkyl substituted with 0–2 $R^8$,
$C_6-C_{10}$ bicycloalkyl substituted with 0–2 $R^8$, benzyl.
aryl substituted with 0–2 $R^{13}$,
phenyl—$C_{2-4}$ alkyl and
a heterocylic ring system composed of 5–10 atoms including 1–3 nitrogen, oxygen, or sulfur heteroatoms, optionally substituted with 0–2 $R^{13}$;

$R^{15}$ and $R^{11}$ can alternatively join to form a 5–8 membered carbocyclic ring substituted with 0–2 $R^{13}$, when $R^{17}$ is H;

$R^7$ is independently selected at each occurrence from the group consisting of:
H, $C_{1-8}$ alkyl, Dhenyl, benzyl, phenethyl, phenoxy, benzyloxy,halogen, hydroxy, nitro, cyano, $C_1-C_5$ alkyl, $C_3-C_6$ cycloalkyl, $C_3-C_6$ cycloalkylmethyl, $C_7-C_{10}$ arylalkyl, $C_1-C_4$ alkoxy, —$CO_2R^{20}$, sulfonamide, formyl, $C_3-C_6$ cycloalkoxy, —OC(=O)$R^{20}$, —C(=O)$R^{20}$, —OC(=O)$OR^{20}$, —$OR^{20}$, —$CH_2OR^{20}$, and $C_1-C_4$ alkyl substituted with —$NR^{20}R^{21}$;

$R^8$ is independently selected at each occurrence from the group consisting of:
=O, F, $C_1$, Br, I, —$CF_3$, —CN, —$CO2R^{20}$, —C(=O)$NR^{20}R^{21}$, —$CH_2OR^{20}$, —OC(=O)$R^{20}$, —$CH_2NR^{20}R^{21}$, and —$NR^{20}R^{21}$;

$R^{13}$ is independently selected at each occurrence from the group consisting of:
phenyl, benzyl, phenethyl, phenoxy, benzyloxy, halogen, hydroxy, nitro, cyano, $C_1-C_5$ alkyl, $C_3-C_6$ cycloalkyl, $C_3-C_6$ cycloalkylmethyl, $C7-C_{10}$ arylalkyl, $C_1-C_4$ alkoxy, —$CO_2R^{20}$, sulfonamide, formyl, $C_3-C_6$ cycloalkoxy, —OC(=O)$R^{20}$, —C(=O)$R^{20}$, —OC(=O)$OR^{20}$, —$OR^{20}$, —$CH_2OR^{20}$, and $C_1-C_4$ alkyl (substituted with —$NR^{20}R^{21}$);

$R^{20}$ is independently:
H, $C_1-C_7$ alkyl, aryl, —($C_1-C_6$ alkyl)aryl, or $C_3-C_6$ alkoxyalkyl;

$R^{21}$ is independently:
H, $C_1-C_4$ alkyl, or benzyl;

$R^{11}$ is H or $C_1-C_8$ alkyl;

$R^{12}$ is H or $C_1-C_8$ alkyl;

$R^2$ is H, $C_1-C_8$ alkyl, $C_3-C_6$ cycloalkyl, $C_3-C_6$ cycloalkylmethyl, $C_1-C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, $(CH_2)_sNHC(=NH)(NH_2)$, or $(CH_2)_sNHR^{21}$, wherein s=3–5;

$R^{12}$ and $R^2$ can be taken together to form—$(CH_2)_t$—, wherein t=2–4, or —$CH_2SC(CH_3)_2$—;

$R^3$ is H or $C_1-C_8$ alkyl;

A is selected from the group consisting of:
-$C_1-C_7$ alkyl-,

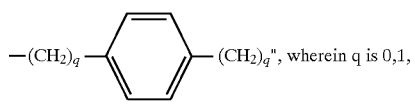

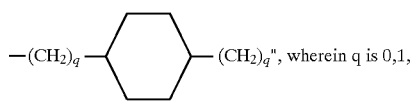

-continued

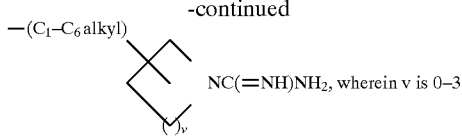
NC(=NH)NH$_2$, wherein v is 0–3 and provided that w=0,
—(CH$_2$)$_m$—O—(C$_{1-4}$ alkyl)—NH—(C$_{1-6}$ alkyl), wherein m=1,2,
—(CH$_2$)$_m$O—(C$_1$–C$_4$ alkyl)—, wherein m=1,2, and
—(CH$_2$)$_m$S—(C$_1$–C$_4$ alkyl)—, wherein m=1,2, R$^3$ and A may also be taken together to form

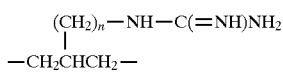

wherein n=0–1 and provided that w=0;
R$^9$ is, H or C$_1$–C$_8$ alkyl;
R$^5$ is, H C$_1$–C$_8$ alkyl; and
R$^{25}$ is t-butyl or benzyl wherein the phenyl ring is substituted with 0–5 C$_1$–C$_4$ alkyl groups, C$_1$–C$_4$ alkoxy groups, or 1–2 halogen atoms.

2. The process of claim 1 wherein:
R$^{19}$ is:

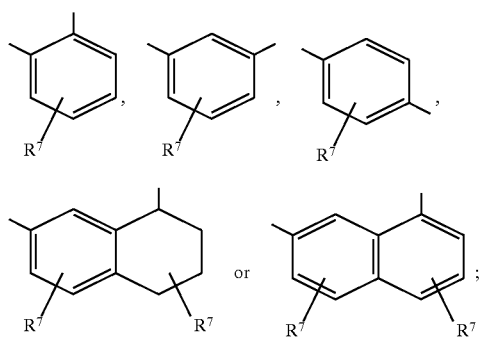

R$^{15}$ and R$^{18}$ are independently selected from H, C$_1$–C$_4$ alkyl, phenyl, benzyl, phenyl-(C$_2$–C$_4$)alkyl, or C$_1$–C$_4$ alkoxy;
R$^{17}$ and R$^{16}$ are independently H or C$_1$–C$_4$ alkyl;
R$^7$ is H, C$_1$–C$_8$ alkyl, phenyl, halogen, or C$_1$–C$_4$ alkoxy;
R$^{11}$ is H or C$_1$–C$_3$ alkyl;
R$^{12}$ is H or CH$_3$;
A is:
C$_1$–C$_7$ alkyl,

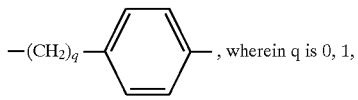, wherein q is 0, 1,

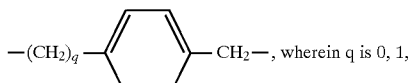, wherein q is 0, 1,

,

-continued
—(CH$_2$)$_m$S(CH$_2$)$_2$—, wherein m = 1, 2,

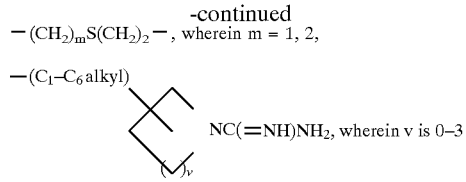
NC(=NH)NH$_2$, wherein v is 0–3 and provided that w=0, or
—(CH$_2$)$_m$—O—(C$_1$–C$_4$ alkyl)—NH—(C$_1$–C$_6$ alkyl), wherein m=1–2, R$^3$ and A may be taken together to form

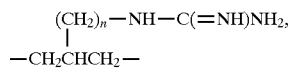

wherein n=0–1 and provided that w=0;
R$^9$ is H or C$_1$–C$_3$ alkyl;
R$^5$ is H or C$_1$–C$_3$ alkyl.

3. The process of claim 2 wherein:
Z=benzyl;
Y=tosyl;
G=CBz;
R$^5$, R$^9$, R$^{16}$, R$^{17}$ and R$^{18}$ are H;
R$^{11}$, R$^{12}$, and R$^{14}$ are H or CH$_3$;
R$^{15}$ is H, C$_1$–C$_4$ alkyl, phenyl, benzyl, or phenyl-(C$_2$–C$_4$) alkyl; and
R$^3$ is H or C$_1$–C$_3$ alkyl.

4. The process of claim 1 wherein:
w is 1;
p is 0;
R$^{19}$ is

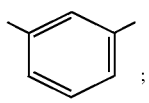;

R$^5$, R$^9$, R$^{17}$, R$^{15}$, R$^{11}$, R$^{12}$, R$^{14}$ are H;
R$^2$ is C$_2$H$_5$;
R$^3$ is CH$_3$; and
A is —(CH$_2$)$_3$—.

5. A process for the preparation of a compound of

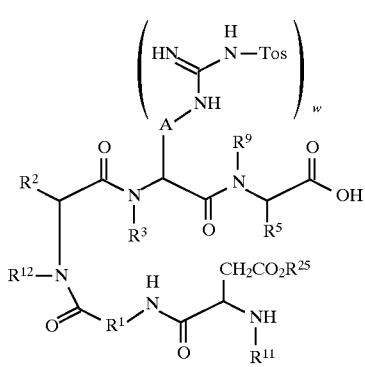

33 comprising cyclizing a compound of formula:

$$\left( \begin{array}{c} H \\ HN \diagdown \diagup N-Tos \\ \diagup NH \\ A \end{array} \right)_w$$

[structure with R², R³, R⁹, R⁵, R¹¹, R¹², R¹, R²⁵, OH, CH₂CO₂R²⁵ groups]

wherein:
  w is 0 or 1;
  R¹ is

[structure with R¹⁹, R¹⁸, R¹⁶, R¹⁷, R¹⁵, p, p']

wherein:
  p and p' are 0 or 1;
  $R^{19}$ is a $C_6$–$C_{14}$ saturated, partially saturated, or aromatic carbocyclic ring system or heterocyclic ring system composed of at least 1–3 heteroatoms selected from N, O, S; all these ring systems may be optionally substituted with 0–2 $R^7$;
  $R^{17}$ and $R^{16}$ are independently:
    hydrogen;
    $C_1$–$C_4$ alkyl, optionally substituted with halogen;
    $C_1$–$C_2$ alkoxy; or
    benzyl;
  $R^{15}$ and $R^{18}$ are independently;
    hydrogen,
    $C_{1-4}$ alkoxy
    $C_1$–$C_8$ alkyl substituted with 0–2 $R^8$,
    $C_2$–$C_8$ alkenyl substituted with 0–2 $R^8$,
    $C_2$–$C_8$ alkynyl substituted with 0–2 $R^8$,
    $C_3$–$C_8$ cycloalkyl substituted with 0–2 $R^8$,
    $C_6$–$C_{10}$ bicycloalkyl substituted with 0–2 $R^8$,
    benzyl,
    aryl substituted with 0–2 $R^{13}$,
    phenyl—$C_{2-4}$ alkyl or
    a heterocylic ring system composed of 5–10 atoms including 1–3 nitrogen, oxygen, or sulfur heteroatoms, optionally substituted with 0–2 $R^{13}$;
  $R^{15}$ and $R^{17}$ can alternatively join to form a 5–7 membered carbocyclic ring substituted with 0–2 $R^{13}$;
  $R^{18}$ and $R^{16}$ can alternatively join to form a 5–7 membered carbocyclic ring substituted with 0–2 $R^{13}$;
  $R^{15}$ and $R^{11}$ can alternatively join to form a 5–8 membered carbocyclic ring substituted with 0–2 $R^{13}$, when $R^{17}$ is H;
  $R^7$ is independently;
    H, $C_{1-8}$ alkyl, phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2R^{20}$, sulfonamide, formyl, $C_3$–$C_6$ cycloalkoxy, —OC(=O)$R^{20}$, —C(=O)$R^{20}$, —OC(=O)O$R^{20}$, —O$R^{20}$, —$CH_2OR^{20}$, or $C_1$–$C_4$ alkyl substituted with —$NR^{20}R^{21}$;

34

$R^8$ is independently;
    =O, F, Cl, Br, I, —$CF_3$, —CN, —$CO_2R^{20}$, —C(=O)$NR^{20}OR^{21}$, —$CH_2OR^{20}$, —OC(=O)$R^{20}$, —$CH_2NR^{20}R^{21}$, or —$NR^{20}R^{21}$;
  $R^{13}$ is independently;
    phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2R^{20}$, sulfonamide, formyl, $C_3$–$C_6$ cycloalkoxy, —OC(=O)$R^{20}$, —C(=O)$R^{20}$, —OC(=O)O$R^{20}$, —O$R^{20}$, —$CH_2OR^{20}$, or $C_1$–$C_4$ alkyl (substituted with —$NR^{20}R^{21}$);
  $R^{20}$ is independently;
    H, $C_1$–$C_7$ alkyl, aryl, —($C_1$–$C_6$ alkyl)aryl, or $C_3$–$C_6$ alkoxyalkyl;
  $R^{21}$ is independently;
    H, $C_1$–$C_4$ alkyl, or benzyl;
  $R^{11}$ is H, or $C_1$–$C_8$ alkyl;
  $R^{12}$ is H, or $C_1$–$C_8$ alkyl;
  $R^2$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, $(CH_2)_sNHC(=NH)(NH_2)$, or $(CH_2)_sNHR^{21}$, wherein s=3–5;
  $R^{12}$ and $R^2$ can be taken together to form —$(CH_2)_t$—, wherein t=2–4, or —$CH_2SC(CH_3)_2$—;
  $R^3$ is H or $C_1$–$C_8$ alkyl;
  A is:
    —$C_1$–$C_7$ alkyl—, —$(CH_2)_q$—[phenylene]—$(CH_2)_{q''}$, wherein q is 0, 1, —$(CH_2)_q$—[cyclohexylene]—$(CH_2)_{q''}$, wherein q is 0, 1, or —($C_1$–$C_6$ alkyl)[ring]$_v$ NC(=NH)NHTos, wherein v is 0–3 and provided that w=0,
  $R^3$ and A may be taken together to form $(CH_2)_n$—NH—C(=NH)NHTos
    |
    —$CH_2CHCH_2$—     , wherein n=0–1 and provided that w=0;
  $R^9$ is H, or $C_1$–$C_8$ alkyl;
  $R^5$ is H, or $C_1$–$C_8$ alkyl; and
  $R^{25}$ is t-butyl or benzyl wherein the phenyl ring is substituted with 0–5 $C_1$–$C_4$ alkyl groups, $C_1$–$C_4$ alkoxy groups, or 1–2 halogen atoms.
6. The process of claim 5 wherein:

$R^{19}$ is:

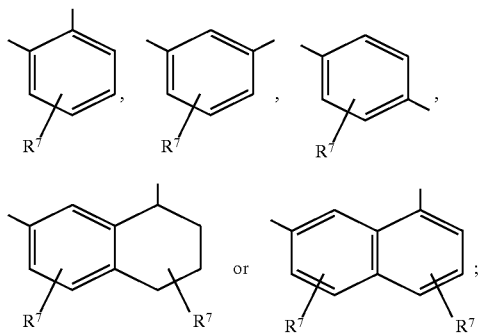

$R^{15}$ and $R^{18}$ are independently H, $C_1$–$C_4$ alkyl, phenyl, benzyl, phenyl-($C_2$–$C_4$)alkyl, or $C_1$–$C_4$ alkoxy;

$R^{17}$ and $R^{16}$ are independently H or $C_1$–$C_4$ alkyl;

$R^7$ is H, $C_1$–$C_8$ alkyl, phenyl, halogen, or $C_1$–$C_4$ alkoxy;

$R^{11}$ is H or $C_1$–$C_3$ alkyl;

$R^{12}$ is H or $CH_3$;

A is:

—$C_1$–$C_7$ alkyl—,

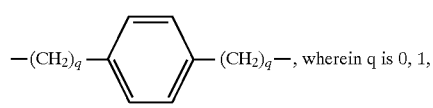, wherein q is 0, 1,

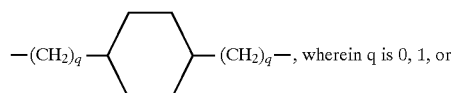, wherein q is 0, 1, or

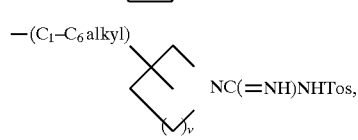

wherein v is 0–3 and provided that w=0, $R^3$ and A may be taken together to form

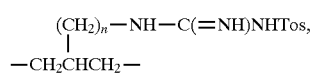

wherein n=0–1 and provided that w=0;

$R^9$ is H or $C_1$–$C_3$ alkyl; and $R^5$ is H or $C_1$–$C_3$ alkyl.

7. The process of claim 6 wherein:

$R^5$, $R^9$, $R^{16}$, $R^{17}$ and $R^{18}$ are H;

$R^{11}$, $R^{12}$, and $R^{14}$ are H or $CH_3$;

$R^{15}$ is H, $C_1$–$C_4$ alkyl, phenyl, benzyl, or phenyl-($C_2$–$C_4$) alkyl; and $R^3$ is H or $C_1$–$C_3$ alkyl.

8. The process of claim 7 wherein:

w is 1;

p is 0;

$R^{19}$ is

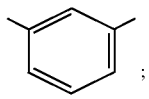

$R^5$, $R^9$, $R^{17}$, $R^{15}$, $R^{11}$, $R^{12}$, $R^{14}$ are H;

$R^2$ is $C_2H_5$;

$R^3$ is $CH_3$; and

A is —$(CH_2)_3$—.

9. The compounds of formula:

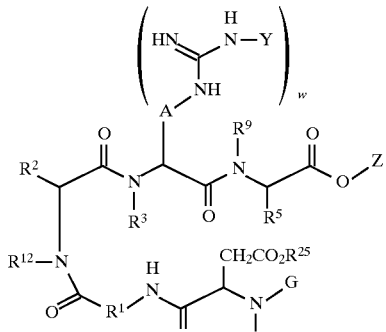

Formula III

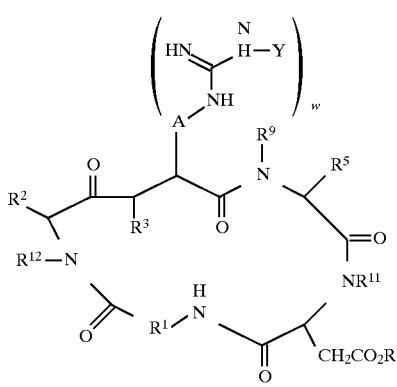

Formula IV wherein:

w=0 or 1;

Y is H or tosyl;

Z is H or benzyl;

G is H or CBZ;

$R^1$ is

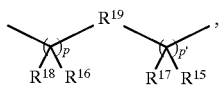

wherein p and p' are 0 or 1;

$R^{19}$ is a $C_6$–$C14$ saturated, partially saturated, or aromatic carbocyclic ring system; all these ring systems are substituted with 0–2 $R^7$;

$R^{17}$ and $R^{16}$ are independently:
hydrogen;
$C_1$–$C_4$ alkyl, optionally substituted with halogen;
$C_1$–$C_2$ alkoxy; or
benzyl;

$R^{15}$ and $R^{18}$ are independently;
hydrogen,
$C_{1-4}$ alkoxy $C_1$–$C_8$ alkyl substituted with 0–2 $R^8$,
$C_2$–$C_8$ alkenyl substituted with 0–2 $R^8$,
$C_2$–$C_8$ alkynyl substituted with 0–2 $R^8$,
$C_3$–$C_8$ cycloalkyl substituted with 0–2 $R^8$,
$C_6$–$C_{10}$ bicycloalkyl substituted with 0–2 $R^8$,
benzyl,
aryl substituted with 0–2 $R^{13}$,
phenyl-$C_{2-4}$ alkyl or
a heterocylic ring system composed of 5–10 atoms including 1–3 nitrogen, oxygen, or sulfur heteroatoms, optionally substituted with 0–2 $R^{13}$;

$R^{15}$ and $R^{17}$ can alternatively join to form a 5–7 membered carbocyclic ring substituted with 0–2 $R^{13}$;

$R^{18}$ and $R^{16}$ can alternatively join to form a 5–7 membered carbocyclic ring substituted with 0–2 $R^{13}$;

$R^{15}$ and $R^{11}$ can alternatively join to form a 5–8 membered carbocyclic ring substituted with 0–2 $R^{13}$, when $R^{17}$ is H;

$R^7$ is independently;
  H, $C_{1-8}$ alkyl, phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2R^{20}$, sulfonamide, formyl, $C_3$–$C_6$ cycloalkoxy, —OC(=O)$R^{20}$, —C(=O)$R^{20}$, —OC(—O)O$R^{20}$, —O$R^{20}$, —$CH_2OR^{20}$, or $C_1$–$C_4$ alkyl substituted with —$NR^{20}R^{21}$;

$R^8$ is independently;
  =O, F, Cl, Br, I, —$CF_3$, —CN, —$CO_2R^{20}$, —C(=O)$NR^{20}R^{21}$, —$CH_2OR^{20}$, —OC(=O)$R^{20}$, —$CH_2NR^{20}R^{21}$, or —$NR^{20}R^{21}$;

$R^{13}$ is independently;
  phenyl, benzyl, phenethyl, phenoxy, benzyloxy, halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2R^{20}$, sulfonamide, formyl, $C_3$–$C_6$ cycloalkoxy, —OC(=O)$R^{20}$, —C(=O)$R^{20}$, —C(=O)O$R^{20}$, —O$R^{20}$, —$CH_2OR^{20}$, or $C_1$–$C_4$ alkyl (substituted with —$NR^{20}R^{21}$);

$R^{20}$ is independently;
  H, $C_1$–$C_7$ alkyl, aryl, —($C_1$–$C_6$ alkyl)aryl, or $C_3$–$C_6$ alkoxyalkyl;

$R^{21}$ is independently;
  H, $C_1$–$C_4$ alkyl, or benzyl;

$R^{11}$ is H or $C_1$–$C_8$ alkyl;
$R^{12}$ is H or $C_1$–$C_8$ alkyl;
$R^2$ is H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, $(CH_2)_sNHC(=NH)(NH_2)$, or $(CH_2)_sNHR^{21}$, wherein s=3–5;

$R^{12}$ and $R^2$ can be taken together to form —$(CH_2)_t$—, wherein t=2–4, or —$CH_2SC(CH_3)_2$—;

$R^3$ is H or $C_1$–$C_8$ alkyl;
A is:
  —$C_1$–$C_7$ alkyl—,

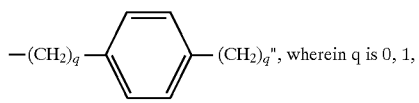, wherein q is 0, 1,

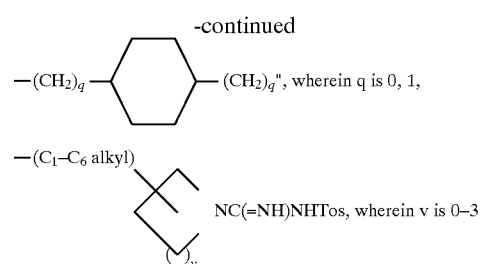, wherein q is 0, 1,

—($C_1$–$C_6$ alkyl)

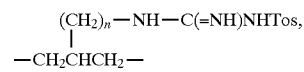 NC(=NH)NHTos, wherein v is 0–3 and provided that w=0,
—$(CH_2)_mO$—($C_1$–$C_4$ alkyl)—, wherein m=1,2, or
—$(CH_2)_mS$—($C_1$–$C_4$ alkyl)—, wherein m=1,2, $R^3$ and A may also be taken together to form $(CH_2)_n$—NH—C(=NH)NHTos,
|
—$CH_2CHCH_2$— wherein n=0–1 and w=0;
$R^9$ is H or $C_1$–$C_8$ alkyl;
$R^5$ is H or $C_1$–$C_8$ alkyl; and
$R^{25}$ is t-butyl or benzyl wherein the phenyl ring is substituted with 0–5 $C_1$–$C_4$ alkyl groups, $C_1$–$C_4$ alkoxy groups, or 1–2 halogen atoms.

10. The compounds of claim 9 wherein:
Y is H or tosyl;
Z is H or benzyl;
G is H or CBZ;
$R^{19}$ is:

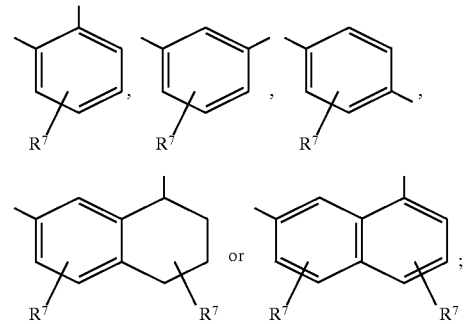

$R^{15}$ and $R^{18}$ are independently H, $C_1$–$C_4$ alkyl, phenyl, benzyl, phenyl-($C_2$–$C_4$)alkyl, or $C_1$–$C_4$ alkoxy;
$R^{17}$ and $R^{16}$ are independently H or $C_1$–$C_4$ alkyl;
$R^7$ is H, $C_1$–$C_8$ alkyl, phenyl, halogen, or $C_1$–$C_4$ alkoxy;
$R^{11}$ is H or $C_1$–$C_3$ alkyl;
$R^{12}$ is H or $CH_3$;
A is:
  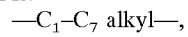

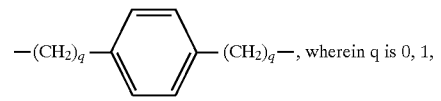, wherein q is 0, 1,

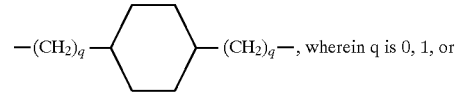, wherein q is 0, 1, or

-continued

—(C₁–C₆alkyl) 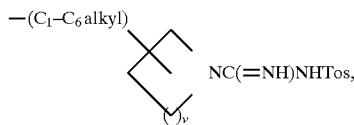 NC(=NH)NHTos, wherein v is 0–3 and provided that w=0,

R³ and A may be taken together to form

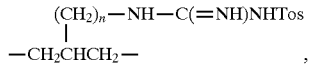

10 wherein n 0–1 and provided that w=0;

$R^9$ is H or $C_1$–$C_3$ alkyl; and $R^5$ is H or $C_1$–$C_3$ alkyl.

11. The compounds of claim 10 wherein:

$R^5$, $R^9$, $R^{16}$, $R^{17}$ and $R^{18}$ are H;

$R^{11}$, $R^{12}$, and $R^{14}$ are H or $CH_3$;

$R^{15}$ is H, $C_1$–$C_4$ alkyl, phenyl, benzyl, or phenyl-($C_2$–$C_4$) alkyl; and $R^3$ is H or $C_1$–$C_3$ alkyl.

12. The compounds of claim 11 wherein:

w is 1;

p is 0;

$R^{19}$ is

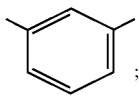

$R^5$, $R^9$, $R^{17}$, $R^{15}$, $R^{11}$, $R^{12}$, $R^{14}$ are H;

$R^2$ is $C_2H_5$;

$R^3$ is $CH_3$; and

A is —$(CH_2)_3$—.

13. A process for the preparation of a compound of formula:

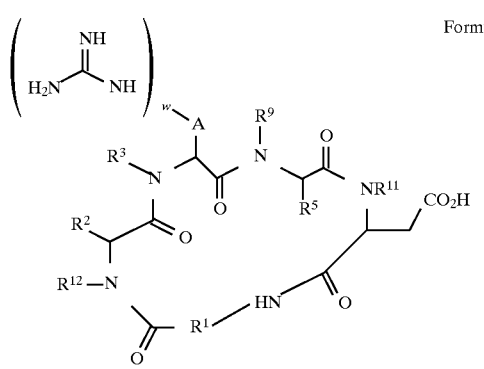

Formula (I)

comprising reacting a compound of Formula:

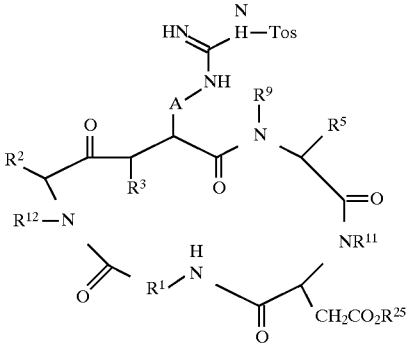

with (a) trifluoracetic acid, (b) triflic acid and (c) anisole, wherein:

w is 0 or 1;

$R^1$ is

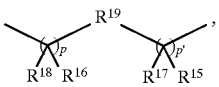

wherein p and p' are 0 or 1'

$R^{19}$ is a $C_6$–$C_{14}$ saturated, partially saturated, or aromatic carbocyclic ring system or heterocyclic ring system composed of at least 1–3 heteroatoms selected from N, O, S; all these ring systems may be optionally substituted with 0–2 $R^7$;

$R^{17}$ and $R^{16}$ are independently:
hydrogen;
$C_1$–$C_4$ alkyl, optionally substituted with halogen;
$C_1$–$C_2$ alkoxy; or
benzyl;

$R^{15}$ and $R^{18}$ are independently;
hydrogen,
$C_{1-4}$ alkoxy
$C_1$–$C_8$ alkyl substituted with 0–2 $R^8$,
$C_2$–$C_8$ alkenyl substituted with 0–2 $R^8$,
$C_2$–$C_8$ alkynyl substituted with 0–2 $R^8$,
$C_3$–$C_8$ cycloalkyl substituted with 0–2 $R^8$,
$C_6$–$C_{10}$ bicycloalkyl substituted with 0–2 $R^8$,
benzyl.
aryl substituted with 0–2 $R^{13}$, phenyl-$C_{2-4}$ alkyl or
a heterocylic ring system composed of 5–10 atoms including 1–3 nitrogen, oxygen, or sulfur heteroatoms, optionally substituted with 0–2 $R^{13}$;

$R^{15}$ and $R^{11}$ can alternatively join to form a 5–8 membered carbocyclic ring substituted with 0–2 $R^{13}$, when $R^{17}$ is H;

$R^7$ is independently:
H, $C_1$-8 alkvl. phenyl, benzyl, phenethyl, phenoxy, benzyloxy,halogen, hydroxy, nitro, cyano, $C_1$–$C_5$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2R^{20}$, sulfonamide, formyl, $C_3$–$C_6$ cycloalkoxy, —OC(=O)$R^{20}$, —C(=O)$R^{20}$, —OC(=O)O$R^{20}$, —O$R^{20}$, —$CH_2OR^{20}$, or $C_1$–$C_4$ alkyl substituted with —N$R^{20}R^{21}$;

$R^8$ is independently:

=O, F, Cl, Br, I, —CF$_3$, —CN, —CO$_2$R$^{20}$, —C(=O)NR$^{20}$R$^{21}$, —CH$_2$OR$^{20}$, —OC(=O)R$^{20}$, —CH$_2$NR$^{20}$R$^{21}$, or —NR$^{20}$R$^{21}$;

R$^{13}$ is independently;
  phenyl, benzyl, phenethyl, phenoxy, benzyloxy, halogen, hydroxy, nitro, cyano, C$_1$–C$_5$ alkyl, C$_3$–C$_6$ cycloalkyl, C$_3$–C$_6$ cycloalkylmethyl, C$_7$–C$_{10}$ arylalkyl, C$_1$–C$_4$ alkoxy, —CO$_2$R$^{20}$, sulfonamide, formyl, C$_3$–C$_6$ cycloalkoxy, —OC(=O)R$^{20}$, —C(=O)R$^{20}$, —OC(=O)OR$^{20}$, —OR$^{20}$, —CH$_2$OR$^{20}$, or C$_1$–C$_4$ alkyl (substituted with —NR$^{20}$R$^{21}$);

R$^{20}$ is independently:
  H, C$_1$–C$_7$ alkyl, aryl, —(C$_1$–C$_6$ alkyl)aryl, or C$_3$–C$_6$ alkoxyalkyl;

R$^{21}$ is independently:
  H, C$_1$–C$_4$ alkyl, or benzyl;

R$^{11}$ is H or C$_1$–C$_8$ alkyl;

R$^{12}$ is H or C$_1$–C$_8$ alkyl;

R$^{2}$ is H, C$_1$–C$_8$ alkyl, C$_3$–C$_6$ cycloalkyl, C$_3$–C$_6$ cycloalkylmethyl, C$_1$–C$_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, CH$_s$NH$_2$, (CH$_2$)$_s$NHC(=NH)(NH$_2$), (CH$_2$)$_s$NHR$^{21}$, wherein s=3–5;

R$^{12}$ and R$^{2}$ can be taken together to form —(CH$_2$)$_t$—, wherein t=2–4, or —CH$_2$SC(CH$_3$)$_2$—;

R$^{3}$ is H or C$_1$–C$_8$ alkyl;

A is:
  -C$_1$–C$_7$ alkyl-,

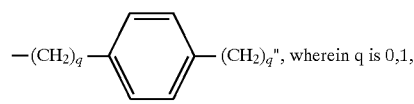, wherein q is 0,1,

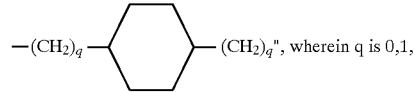, wherein q is 0,1,

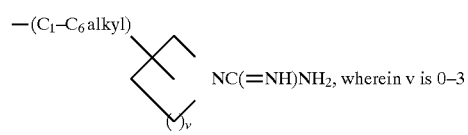 NC(=NH)NH$_2$, wherein v is 0–3 and provided that w=0,
—(CH$_2$)$_m$—O—(C$_{1-4}$ alkyl)—Nh—(C$_{1-6}$ alkyl), wherein m=1,2
—(CH$_2$)$_m$O—(C$_1$–C$_4$ alkyl)—, wherein m=1,2, or
—(CH$_2$)$_m$S—(C$_1$–C$_4$ alkyl)—, wherein m=1,2, R$^{3}$ and A may also be taken together to form

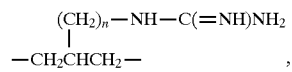, wherein n=0–1 and provided that w=0;

R$^{9}$ is H or C$_1$–C$_8$ alkyl;

R$^{5}$ is H or C$_1$–C$_8$ alkyl; and

R$^{25}$ is t-butyl or benzyl wherein the phenyl ring is substituted with 0–5 C$_1$–C$_4$ alkyl groups, C$_1$–C$_4$ alkoxy groups, or 1–2 halogen atoms.

14. The process of claim 13 wherein:

R$^{19}$ is:

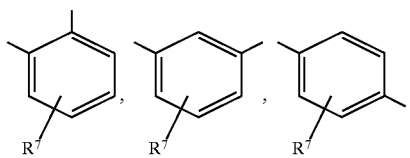

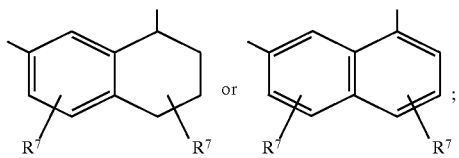

R$^{15}$ and R$^{18}$ are independently H, C$_1$–C$_4$ alkyl, phenyl, benzyl, phenyl-(C$_2$–C$_4$)alkyl, or C$_1$–C$_4$ alkoxy;

R$^{17}$ and R$^{16}$ are independently H or C$_1$–C$_4$ alkyl;

R$^{7}$ is H, C$_1$–C$_8$ alkyl, phenyl, halogen, or C$_1$–C$_4$ alkoxy;

R$^{11}$ is H or C$_1$–C$_3$ alkyl;

R$^{12}$ is H or CH$_3$;

A is selected from the group:
  C$_1$–C$_7$ alkyl,

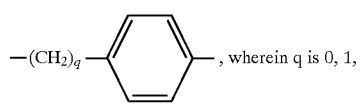, wherein q is 0, 1,

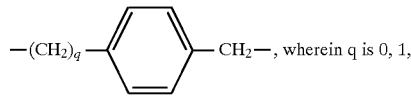, wherein q is 0, 1,

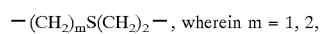, wherein m = 1, 2,

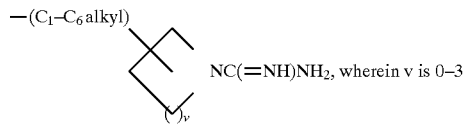 NC(=NH)NH$_2$, wherein v is 0–3 and provided that w=0, or
—(CH$_2$)$_m$—O—(C$_1$–C$_4$ alkyl)—NH—(C$_1$–C$_6$ alkyl), wherein m=1–2, R$^{3}$ and A may be taken together to form

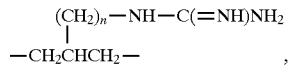, wherein n=0–1 and provided that w=0;

R$^{9}$ is H or C$_1$–C$_3$ alkyl; and

R$^{5}$ is H or C$_1$–C$_3$ alkyl.

15. The process of claim 14 wherein:

R$^{5}$, R$^{9}$, R$^{16}$, R$^{17}$ and R$^{18}$ are H;

R$^{11}$, R$^{12}$, and R$^{14}$ are H or CH$_3$;

R$^{15}$ is H, C$_1$–C$_4$ alkyl, phenyl, benzyl, or phenyl-(C$_2$–C$_4$) alkyl; and R$^{3}$ is H or C$_1$–C$_3$ alkyl.

16. The process of claim 15 wherein:

w is 1;

p is 0;
R$^{19}$ is

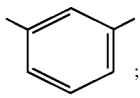;

R$^5$, R$^9$, R$^{17}$, R$^{15}$, R$^{11}$, R$^{12}$, R$^{14}$ are H;
R$^2$ is C$_2$H$_5$;
R$^3$ is CH$_3$; and
A is —(CH$_2$)$_3$—.

17. The process of claims any of 13–16 wherein trifluoroacetic acid, triflic acid, and anisole are added sequentially.

18. The process of claims any of 13–16 wherein trifluoroacetic acid is ommitted.

19. The compounds of formula:

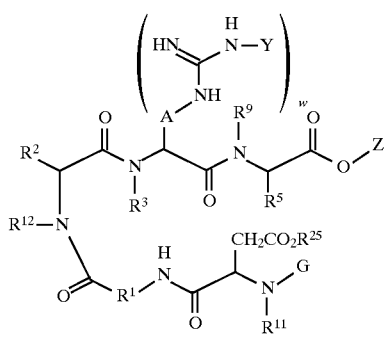

Formula III wherein:
w=0 or 1;
Y is H or tosyl;
Z is H or benzyl;
G is H or CBZ;

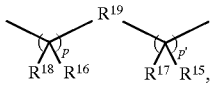

R$^1$ is
 wherein
 p and p' are 0 or 1;
 R$^{19}$ is a heterocyclic ring system composed of at least 1–3 heteroatoms selected from N, O, S; all these ring systems are substituted with 0–2 R$^7$;
 R$^{17}$ and R$^{16}$ are independently:
  hydrogen;
  C$_1$–C$_4$ alkyl, optionally substituted with halogen;
  C$_1$–C$_2$ alkoxy; or
  benzyl;
 R$^{15}$ and R$^{18}$ are independently;
  hydrogen,
  C$_{1-4}$ alkoxy
  C$_1$–C$_8$ alkyl substituted with 0–2 R$^8$,
  C$_2$–C$_8$ alkenyl substituted with 0–2 R$^8$,
  C$_2$–C$_8$ alkynyl substituted with 0–2 R$^8$,
  C$_3$–C$_8$ cycloalkyl substituted with 0–2 R$^8$,
  C$_6$–C$_{10}$ bicycloalkyl substituted with 0–2 R$^8$,
  benzyl,
  aryl substituted with 0–2 R$^{13}$,
  phenyl—C$_{2-4}$ alkyl
  a heterocylic ring system composed of 5–10 atoms including 1–3 nitrogen, oxygen, or sulfur heteroatoms, optionally substituted with 0–2 R$^{13}$;

R$^{15}$ and R$^{17}$ can alternatively join to form a 5–7 membered carbocyclic ring substituted with 0–2 R$^{13}$;
R$^{18}$ and R$^{16}$ can alternatively join to form a 5–7 membered carbocyclic ring substituted with 0–2 R$^{13}$;
R$^{15}$ and R$^{11}$ can alternatively join to form a 5–8 membered carbocyclic ring substituted with 0–2 R$^{13}$, when R$^{17}$ is H;
R$^7$ is independently;
 H, C$_{1-8}$ alkyl, phenyl, benzyl, phenethyl, phenoxy, benzyloxy,halogen, hydroxy, nitro, cyano, C$_1$–C$_5$ alkyl, C$_3$–C$_6$ cycloalkyl, C$_3$–C$_6$ cycloalkylmethyl, C7–C$_{10}$ arylalkyl, C$_1$–C$_4$ alkoxy, —CO$_2$R$^{20}$, sulfonamide, formyl, C$_3$–C$_6$ cycloalkoxy, —OC(=O)R$^{20}$, —C(=O)R$^{20}$, —OC(—O)OR$^{20}$, —OR$^{20}$, —CH$_2$OR$^{20}$, or C$_1$–C$_4$ alkyl substituted with —NR$^{20}$OR$^{21}$;
R$^8$ is independently;
 =O, F, Cl, Br, I, —CF$_3$, —CN, —CO$_2$R$^{20}$, —C(=O)NR$^{20}$R$^{21}$, —CH$_2$OR$^{20}$, —OC(=O)R$^{20}$, —CH$_2$NR$^{20}$R$^{21}$, or —NR$^{20}$R$^{21}$;
R$^{13}$ is independently;
 phenyl, benzyl, phenethyl, phenoxy, benzyloxy, halogen, hydroxy, nitro, cyano, C$_1$–C$_5$ alkyl, C$_3$–C$_6$ cycloalkyl, C$_3$–C$_6$ cycloalkylmethyl, C$_7$–C$_{10}$ arylalkyl, C$_1$–C$_4$ alkoxy, —CO$_2$R$^{20}$, sulfonamide, formyl, C$_3$–C$_6$ cycloalkoxy, —OC(=O)R$^{20}$, —C(=O)R$^{20}$, —OC(=O)OR$^{20}$, —OR$^{20}$, —CH$_2$OR$^{20}$, or C$_1$–C$_4$ alkyl (substituted with —NR$^{20}$R$^{21}$);
R$^{20}$ is independently;
 H, C$_1$–C$_7$ alkyl, aryl, —(C$_1$–C$_6$ alkyl)aryl, or C$_3$–C$_6$ alkoxyalkyl;
R$^{21}$ is independently;
 H, C$_1$–C$_4$ alkyl, or benzyl;
R$^{11}$ is H or C$_1$–C$_8$ alkyl;
R$^{12}$ is H or C$_1$–C$_8$ alkyl;
R$^2$ is H, C$_1$–C$_8$ alkyl, C$_3$–C$_6$ cycloalkyl, C$_3$–C$_6$ cycloalkylmethyl, C$_1$–C$_6$ cycloalkylethyl, phenyl, phenylmethyl, CH$_2$OH, CH$_2$SH, CH$_2$OCH$_3$, CH$_2$SCH$_3$, CH$_2$CH$_2$SCH$_3$, or (CH$_2$)sNH2, (CH$_2$)$_s$NHC(=NH)(NH2), (CH$_2$)$_s$NHR$^{21}$, wherein s=3–5;
R$^{12}$ and R$^2$ can be taken together to form —(CH$_2$)$_t$—, wherein t=2–4, or —CH$_2$SC(CH$_3$)$_2$—;
R$^3$ is H or C$_1$–C$_8$ alkyl;
A is selected from the group:
 -C$_1$–C$_7$ alkyl-,

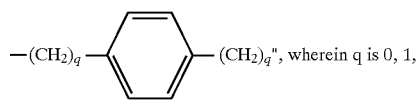, wherein q is 0, 1,

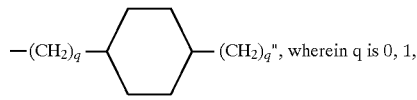, wherein q is 0, 1,

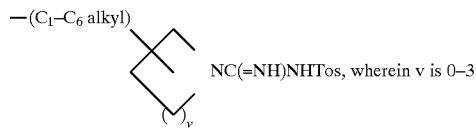 NC(=NH)NHTos, wherein v is 0–3 and provided that w=0,
—(CH$_2$)$_m$O—(C$_1$–C$_4$ alkyl)—, wherein m=1,2, or
—(CH$_2$)$_m$S—(C$_1$–C$_4$ alkyl)—, wherein m=1,2, $R^3$ and A may also be taken together to form
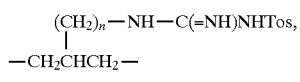
wherein n=0–1 and w=0;
$R^9$ is H, $C_1$–$C_8$ alkyl;
$R^5$ is H, $C_1$–$C_8$ alkyl; and
$R^{25}$ is t-butyl or benzyl wherein the phenyl ring is substituted with 0–5 $C_1$–$C_4$ alkyl groups, $C_1$–$C_4$ alkoxy groups, or 1–2 halogen atoms.
* * * * *